US011981927B2

(12) United States Patent
Suzuki

(10) Patent No.: US 11,981,927 B2
(45) Date of Patent: May 14, 2024

(54) METHOD FOR PRODUCING LIVER STEM CELLS OR LIVER PROGENITOR CELLS BY DIRECT REPROGRAMMING

(71) Applicant: KYUSHU UNIVERSITY, NATIONAL UNIVERSITY CORPORATION, Fukuoka (JP)

(72) Inventor: Atsushi Suzuki, Fukuoka (JP)

(73) Assignee: KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 620 days.

(21) Appl. No.: 16/757,817

(22) PCT Filed: Oct. 23, 2018

(86) PCT No.: PCT/JP2018/039295
§ 371 (c)(1),
(2) Date: Apr. 21, 2020

(87) PCT Pub. No.: WO2019/082874
PCT Pub. Date: May 2, 2019

(65) Prior Publication Data

US 2021/0189347 A1 Jun. 24, 2021

(30) Foreign Application Priority Data

Oct. 23, 2017 (JP) ................................ 2017-204432

(51) Int. Cl.
*C12N 5/071* (2010.01)

(52) U.S. Cl.
CPC ........ *C12N 5/0672* (2013.01); *C12N 2501/10* (2013.01); *C12N 2506/11* (2013.01); *C12N 2506/28* (2013.01)

(58) Field of Classification Search
CPC .................................................. C12N 5/0672
See application file for complete search history.

(56) References Cited

U.S. PATENT DOCUMENTS

| | | | |
|---|---|---|---|
| 2012/0231490 | A1 | 9/2012 | Mizuguchi et al. |
| 2014/0087416 | A1 | 3/2014 | Simeonov et al. |
| 2017/0218333 | A1 | 8/2017 | Deng et al. |

FOREIGN PATENT DOCUMENTS

| | | | |
|---|---|---|---|
| JP | 2015-527084 | A | 9/2015 |
| JP | 2016-10379 | A | 1/2016 |
| JP | 2017-511150 | A | 4/2017 |
| WO | WO 2011/052504 | A1 | 5/2011 |
| WO | WO. 2013/189521 | A1 | 12/2013 |

OTHER PUBLICATIONS

Eguchi (2016 Stem Cells International Article ID 7530942).*
Mizoshiri (Biochemical and Biophysical Research Communications, vol. 467, No. 4, pp. 1110-1116, 2015).*
Yamamoto (2015, PNAS 112:6152-6157).*
Fagnocchi (Nature Communications, 7:11903, 17 pages).*
Firas (Immunology and Cell Biology, 2015, 93:284-289).*
Qin (Stem Cell Rev and Rep (2016) 12:708-720).*
Zhang (2003 World J. Gastroenterol. 9:201-204).*
Ding et al., "Overexpression of transcription factor Foxa2 and Hnf1α induced rat bone mesenchymal stem cells into hepatocytes," Cytotechnology (2016), vol. 68, pp. 2037-2047.
Du et al., "Human Hepatocytes with Drug Metabolic Function Induced from Fibroblasts by Lineage Reprogramming," Cell Stem Cell (Mar. 6, 2014), vol. 14, pp. 394-403.
Huang et al., "Direct Reprogramming of Human Fibroblasts to Functional and Expandable Hepatocytes," Cell Stem Cell (Mar. 6, 2014), vol. 14, pp. 370-384.
International Search Report dated Jan. 15, 2019, in PCT/JP2018/039295.
Miura, S. and A. Suzuki, "Generation of Mouse and Human Organoid-Forming Intestinal Progenitor Cells by Direct Lineage Reprogramming," Cell Stem Cell (Oct. 5, 2017), vol. 21, pp. 456-471.
Nakagawa et al., "Promotion of direct reprogramming by transformation-deficient Myc," PNAS (Aug. 10, 2010), vol. 107, No. 32, pp. 14152-14157.
Suzuki, A., "Direct reprogramming technology toward medical applications for liver diseases," Jikken-Igaku (2015), vol. 33, No. 2, pp. 72-79, with partial English translation.
Wang et al., "Regulation of transcription factor during liver development," Chemistry of Life (2011), vol. 31, No. 3, pp. 395-400, with abstract.
Yu et al., "Reprogramming Fibroblasts into Bipotential Hepatic Stem Cells by Defined Factors," Cell Stem Cell (Sep. 5, 2013), vol. 13, pp. 328-340.
Extended European Search Report dated Jun. 24, 2021, in European Patent Application No. 18870975.2.

* cited by examiner

*Primary Examiner* — Valarie E Bertoglio
(74) *Attorney, Agent, or Firm* — Birch, Stewart, Kolasch & Birch, LLP

(57) ABSTRACT

A method for inducing conversion from non-hepatic stem cells or non-hepatic progenitor cells into hepatic stem cells or hepatic progenitor cells, which comprises introducing any of the following combinations into the non-hepatic stem cells or non-hepatic progenitor cells:
(a) a combination of HNF1, HNF6 and FOXA;
(b) a combination of HNF1 gene, HNF6 gene and FOXA gene;
(c) a combination of HNF1, MYC and FOXA; or
(d) a combination of HNF1 gene, MYC gene and FOXA gene.

10 Claims, 12 Drawing Sheets

Specification includes a Sequence Listing.

METHOD FOR PRODUCING LIVER STEM CELLS OR LIVER PROGENITOR CELLS BY DIRECT REPROGRAMMING

TECHNICAL FIELD

The present invention relates to a method for producing hepatic stem cells or hepatic progenitor cells by introducing given reprogramming factors into vascular endothelial cells, etc.

BACKGROUND ART

Techniques have already been known to prepare hepatocytes by introducing a certain set of genes into human fibroblasts, as exemplified by a method for preparing induced hepatocytes from non-hepatic cells, in which CEBPA, HNF4A, FOXA3, GATA4, HNF1A and so on are used as reprogramming factors (Patent Document 1: JP 2015-527084 A).

Moreover, it has been known that once mouse embryonic fibroblasts have been transfected with Hnf1β and Foxa3, they will be reprogrammed into hepatic stem cells (Non-patent Document 1), and other methods have also been known, e.g., a method for reprogramming human fibroblasts into mature hepatocytes upon expression of FOXA3, HNF1A and HNF4A (Non-patent Document 2), a method for preparing human induced hepatocytes upon overexpression of HNF1A, HNF4A and HNF6 together with maturation factors ATFS, PROX1 and CEBPA (Non-patent Document 3), etc.

However, hepatocytes induced by these conventional methods are poor in proliferation potency and also cannot differentiate into cholangiocytes.

PRIOR ART DOCUMENTS

Patent Documents

Patent Document 1: JP 2015-527084 A

Non-Patent Documents

Non-patent Document 1: Bing Yu et al., Cell Stem Cell 13, 1-13, Sep. 5, 2013

Non-patent Document 2: Pengyu Huang et al., Cell Stem Cell 14, 1-15, Mar. 6, 2014

Non-patent Document 3: Yuanyuan Du et al., Cell Stem Cell 14, 1-10, Mar. 6, 2014

SUMMARY OF THE INVENTION

Problem to be Solved by the Invention

Once it has been possible to obtain hepatic stem cells or hepatic progenitor cells (hereinafter referred to as hepatic stem/hepatic progenitor cells) which have proliferation potency and are capable of differentiating into cholangiocytes, these cells when cultured will allow the supply of desired hepatocytes or cholangiocytes in an amount enough for the intended purpose. For this reason, there has been a demand for the development of a method for producing hepatic stem/hepatic progenitor cells.

As a result of extensive and intensive efforts made to solve the problem stated above, the inventors of the present invention have succeeded in obtaining hepatic stem/hepatic progenitor cells upon combination of given genes, which in turn led to the completion of the present invention.

Means to Solve the Problem

Namely, the present invention is as follows.

(1) A method for inducing conversion from non-hepatic stem cells or non-hepatic progenitor cells into hepatic stem cells or hepatic progenitor cells, which comprises introducing any of the following combinations into the non-hepatic stem cells or non-hepatic progenitor cells:

- (a) a combination of HNF1, HNF6 and FOXA;
- (b) a combination of HNF1 gene, HNF6 gene and FOXA gene;
- (c) a combination of HNF1, MYC and FOXA; or
- (d) a combination of HNF1 gene, MYC gene and FOXA gene.

(2) A method for producing hepatic stem cells or hepatic progenitor cells, which comprises the step of inducing hepatic stem cells or hepatic progenitor cells by the method according to (1) above.

(3) The method according to (1) or (2) above, wherein HNF1 is HNF1A.

(4) The method according to any one of (1) to (3) above, wherein FOXA is FOXA3.

(5) The method according to any one of (1) to (4) above, wherein the combination is (a) or (b), and MYC or MYC gene is further introduced.

(6) The method according to any one of (1) to (5) above, wherein MYC is L-MYC.

(7) The method according to any one of (1) to (6) above, wherein the non-hepatic stem cells or non-hepatic progenitor cells are vascular endothelial cells or blood-derived cells.

(8) The method according to (7) above, wherein the vascular endothelial cells are derived from umbilical veins, peripheral blood or umbilical cord blood.

(9) The method according to (7) above, wherein the blood-derived cells are peripheral blood T cells or umbilical cord blood T cells.

(10) Hepatic stem cells or hepatic progenitor cells produced by the method according to any one of (2) to (9) above.

(11) A method for producing hepatocytes or cholangiocytes, which comprises the steps of:

- (a) inducing hepatic stem cells or hepatic progenitor cells by the method according to (1) above; and
- (b) allowing the induced hepatic stem cells or hepatic progenitor cells to differentiate into hepatocytes or cholangiocytes.

Effects of the Invention

The present invention provides a method for inducing conversion from any cells other than hepatic stem cells and hepatic progenitor cells, i.e., non-hepatic stem cells or non-hepatic progenitor cells (hereinafter referred to as "non-hepatic stem/non-hepatic progenitor cells") into hepatic stem/hepatic progenitor cells (reprogramming method), and a method for producing hepatic stem/hepatic progenitor cells. The present invention allows direct conversion from non-hepatic stem/non-hepatic progenitor cells (e.g., vascular endothelial cells) into hepatic stem/hepatic progenitor cells. The thus induced hepatic stem/hepatic progenitor cells have long-term proliferation potency and are capable of differentiating into hepatocytes or cholangiocytes. In addition, not only embryonic vascular endothelial cells, but also vascular endothelial cells in adult peripheral blood can be induced into hepatic stem/hepatic progenitor cells. Thus, the present invention also allows liver function test and drug screening with the use of hepatic stem/hepatic progenitor cells derived from peripheral blood.

DESCRIPTION OF EMBODIMENTS

Figure 1:
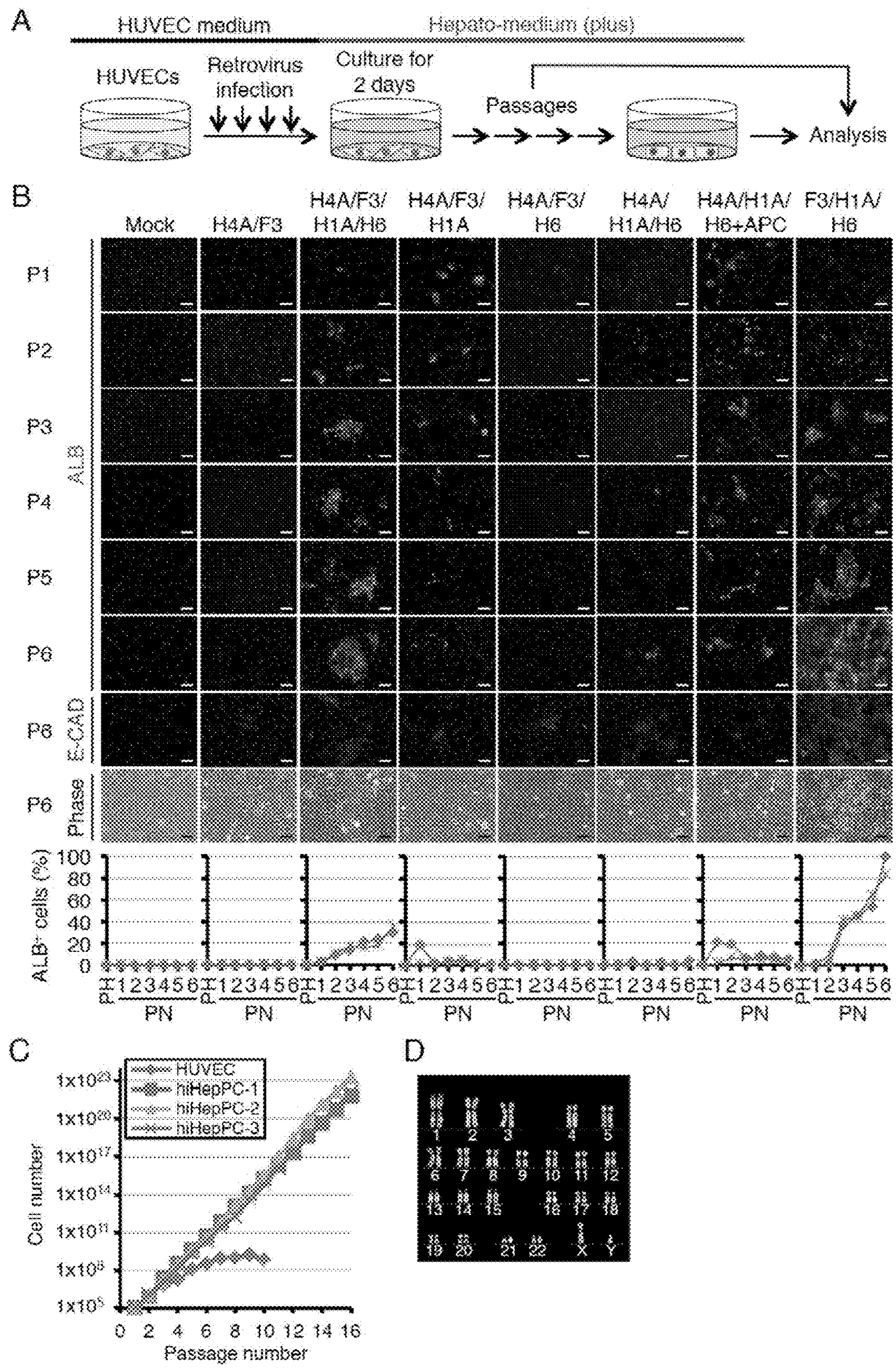
FIG. 1 shows identification of specific factors responsible for inducing human induced hepatic progenitor cells (hiHepPCs).

The present invention relates to a method for inducing conversion from non-hepatic stem/non-hepatic progenitor cells into hepatic stem/hepatic progenitor cells, which comprises introducing a combination of reprogramming factors HNF1A, HNF6 and FOXA, a combination of genes encoding these factors, a combination of reprogramming factors HNF1A, MYC and FOXA or a combination of genes encoding these factors into the non-hepatic stem/non-hepatic progenitor cells. The present invention is not intended to induce cells which have already differentiated, but is characterized by inducing hepatic stem/hepatic progenitor cells, which serve as their origin, from non-hepatic stem/non-hepatic progenitor cells, and is configured to use a combination of reprogramming factors as mentioned above.

1. Non-Hepatic Stem/Non-Hepatic Progenitor Cells

In the present invention, the non-hepatic stem/non-hepatic progenitor cells to be used are intended to mean any cells other than desired hepatic stem/hepatic progenitor cells. Examples of non-hepatic stem/non-hepatic progenitor cells include fibroblasts, endothelial cells, blood cells, umbilical cord blood cells, bone marrow cells, keratinocytes, hepatocytes, cholangiocytes, myofibroblasts, neuronal lineage cells, epithelial lineage cells and so on. In the present invention, vascular endothelial cells or blood-derived cells can be used, by way of example. Examples of vascular endothelial cells include those derived from umbilical veins, peripheral blood or umbilical cord blood, while examples of blood-derived cells include peripheral blood cells or umbilical cord blood cells (e.g., peripheral blood T cells or umbilical cord blood T cells). The non-hepatic stem/non-hepatic progenitor cells to be used in the present invention may be of mammalian origin (e.g., mouse, rat, rabbit, cat, dog, monkey, human). In one embodiment of the present invention, the non-hepatic stem/non-hepatic progenitor cells to be used are those of human origin.

2. Reprogramming Factors

The term "reprogramming" refers to a process that changes the differentiation status of cells to their another differentiation status or their undifferentiated status. In the present invention, the above non-hepatic stem/non-hepatic progenitor cells are induced into hepatic stem/hepatic progenitor cells. In the present invention, non-hepatic stem/non-hepatic progenitor cells can be induced into hepatic stem/hepatic progenitor cells without being converted into pluripotent stem cells. Factors for use in such reprogramming (reprogramming factors) are as shown below:

(a) a combination of HNF1, HNF6 and FOXA;

(b) a combination of HNF1 gene, HNF6 gene and FOXA gene;

(c) a combination of HNF1, MYC and FOXA; or (d) a combination of HNF1 gene, MYC gene and FOXA gene.

HNF1 (Hepatocyte Nuclear Factor 1) is a protein having a homeodomain, and there are two isoforms HNF1A and HNF1B.

HNF6 (Hepatocyte Nuclear Factor 6) is a homeodomain-type transcription factor involved in human tissue development, and is responsible for controlling the development of various tissues including pancreas and liver and is also responsible for controlling the expression of various hepatic genes.

FOXA is a hepatocyte nuclear factor (transcription factor) required during the earliest process of liver tissue formation, and includes FOXA1, FOXA2 and FOXA3. These FOXA transcription factors share 90% or more homology at the amino acid level in their common forkhead/wingedhelix domain, and are therefore deemed to have functional complementarity to each other.

Moreover, in the present invention, if the above combination of reprogramming factors is (a) or (b), L-MYC may further be combined.

MYC family genes are known as transcription factors which work upon binding to nuclear DNA, and there are c-MYC, L-MYC and N-MYC in humans. In the present invention, all of these factors can be used.

Table 1 shows the amino acid sequences of the above reprogramming factors, and the nucleotide sequences of genes encoding these factors.

TABLE 1

| Reprogramming factor | Nucleotide sequence | Amino acid sequence |
|---|---|---|
| HNF1A NM_000545 | SEQ ID NO: 1 | SEQ ID NO: 2 |
| HNF6 NM_004498 | SEQ ID NO: 3 | SEQ ID NO: 4 |
| FOXA1 NM_004496 | SEQ ID NO: 5 | SEQ ID NO: 6 |
| FOXA2 NM_021784 | SEQ ID NO: 7 | SEQ ID NO: 8 |
| FOXA3 NM_004497 | SEQ ID NO: 9 | SEQ ID NO: 10 |
| L-MYC GenBank: M19720.1 | SEQ ID NO: 11 | SEQ ID NO: 12 |

Some of the genes encoding these factors can be cloned by reference to "Molecular Cloning, A Laboratory Manual (4th edition)" (Cold Spring Harbor Laboratory Press (2012)), etc., or may also be available from addgene, etc.

A gene encoding HNF1A is herein referred to as "HNF1A gene" while a gene encoding HNF6 is herein referred to as "HNF6 gene." Genes encoding the other factors are also referred to in the same manner as above.

In one embodiment of the present invention, it is possible to use, for example, the following combination of reprogramming factors or a set of genes encoding these factors:

HNF1A, HNF6 and FOXA3;

HNF1A, L-MYC and FOXA3; or

HNF1A, HNF6, FOXA3 and L-MYC.

The reprogramming factors (genes or proteins) used in the present invention are not limited to the nucleotide sequences and amino acid sequences represented by the SEQ ID NOs shown in Table 1, and may also include the mutants shown below as long as they have the functions as reprogramming factors intended in the present invention:

(a) proteins which consist of amino acid sequences with deletion, substitution or addition of one or several (e.g., 10 or less, 5 or less, 4 or less, 3 or less, or 2) amino acids in the amino acid sequences shown in Table 1 and which have the functions as reprogramming factors intended in the present invention possessed by the respective reprogramming factors;

(b) proteins which consist of amino acid sequences sharing a homology of 80% or more, 85% or more, 90% or more, 95% or more, 98% or more, or 99% or more with the amino acid sequences shown in Table 1 and which have the functions as reprogramming factors intended in the present invention possessed by the respective reprogramming factors;

(c) nucleic acids encoding the proteins shown in (a) above;

(d) nucleic acids encoding the proteins shown in (b) above; and (e) nucleic acids which are hybridizable under stringent conditions with nucleic acids consisting of nucleotide sequences complementary to the nucleotide sequences shown in Table 1 and which encode proteins having the functions as reprogramming factors intended in the present invention possessed by the respective reprogramming factors.

In the present invention, the term "stringent conditions" refers to, for example, conditions of 5×SSC, 5×Denhardt's solution, 0.5% SDS, 50% formamide and 50° C. Under these conditions, it can be expected that DNA and/or RNA having a higher homology is more efficiently obtained at a higher temperature. However, the stringency of hybridization would be affected by a plurality of factors, including temperature, DNA and/or RNA concentration, DNA and/or RNA length, ionic strength, reaction time, salt concentration and so on. Those skilled in the art would be able to achieve the same stringency by selecting these factors as appropriate.

3. Introduction of Reprogramming Factors into Cells

To introduce the reprogramming factors into non-hepatic stem/non-hepatic progenitor cells serving as host cells, a recombinant vector(s) may be constructed to carry genes encoding the reprogramming factors in the same vector or separate vectors. In the present invention, the vector(s) may be constructed by using a replicon which may be inserted to cause the replication of an insert segment. The vector(s) may be constructed as an expression vector(s) in which one or more expression regulatory sequences are operably linked, and may be constructed to comprise DNA(s) for controlling the transcription and/or translation of an additional DNA sequence(s) other than the reprogramming factors. Examples of expression regulatory sequences include a promoter, an enhancer, a transcription terminator and so on.

In the present invention, the genes encoding the reprogramming factors may be inserted as follows: a set of genes to be introduced may all be linked to a single vector or these individual genes may be linked to separate vectors. Alternatively, some of the genes may be linked to a single vector, and the other genes may be linked to other vector(s).

Examples of expression vectors available for use in the present invention include plasmids, bacteriophages, as well as virus vectors derived from retrovirus, vaccinia virus, adenovirus, lentivirus, adeno-associated virus, Sendai virus and other viruses. Such an expression vector may be introduced into non-hepatic stem/non-hepatic progenitor cells in any manner, for example, by infecting the cells with an expression vector(s) comprising genes encoding the respective reprogramming factors. In addition to this, lipofection, electroporation, calcium phosphate transfection or the like may be used for this purpose, by way of example. The dose of the virus vector(s) when infected into the cells may be adjusted as appropriate.

The method of the present invention for inducing conversion from non-hepatic stem/non-hepatic progenitor cells into hepatic stem/hepatic progenitor cells may be carried out either in vitro or in vivo. If the method is carried out in vitro, the expression vector(s) may be introduced into non-hepatic stem/non-hepatic progenitor cells to obtain transformants, which may then be cultured for a given period of time. Culture may be accomplished by using a medium for use in animal cell culture, and subculture may then be repeated as needed to thereby cause reprogramming into hepatic stem/hepatic progenitor cells.

If the method is carried out in vivo, the expression vector(s) may be introduced by any known introduction techniques into non-hepatic stem/non-hepatic progenitor cells in an animal, e.g., through its dermal tissue or via the intravascular or intraperitoneal route to thereby obtain transformants. Then, cells reprogrammed into hepatic stem/hepatic progenitor cells can be confirmed in the animal's tissue or in cells collected from the animal's tissue.

Whether or not the resulting cells were reprogrammed into hepatic stem/hepatic progenitor cells can be confirmed by markers which are expressed in these cells. Examples of such markers include albumin, α-fetoprotein, E-cadherin and so on.

Alternatively, in the present invention, polypeptides of the following factors may also be directly introduced into cells:

HNF1A, HNF6 and FOXA3;

HNF1A, L-MYC and FOXA3; or

HNF1A, HNF6, FOXA3 and L-MYC.

The above factors may be prepared in a genetic engineering manner (see, e.g., "Molecular Cloning, A Laboratory Manual (4th edition)" (Cold Spring Harbor Laboratory Press (2012)) and the resulting polypeptides may be introduced into cells, for example, by being linked to membrane-permeable peptides, etc., or by means of cationic lipids. Moreover, transfection reagents are also commercially available (e.g., PULSin (PPU), Prote-IN (HYG), BioPORTER Protein Delivery Reagent (GTS)).

EXAMPLES

The present invention will be further described in more detail by way of the following illustrative examples, although the scope of the present invention is not limited by these examples.

Example 1

(1) Identification of Specific Factors Responsible for Inducing Human Induced Hepatic Progenitor Cells (hiHepPCs)

FIG. 1A schematically shows the hiHepPC induction experiment.

Commercially available human umbilical vein endothelial cells (HUVECs) were transfected with a retrovirus vector (gene expression vector) through retrovirus infection. During transfection, HUVECs were cultured in a medium (HU- VEC medium) composed of a 1:1 mixture of Medium 200 and Fibrolife serum-free cell culture medium. After virus infection, the cells were cultured for 2 days in a medium (Hepato-medium (plus)) composed of Hepato-medium (i.e., a 1:1 mixed medium of DMEM and F12 supplemented with 4% fetal bovine serum, 1 μg/ml insulin, $10^{-7}$ M dexamethasone, 10 mM nicotinamide, 2 mM L-glutamine, 50 μM β-mercaptoethanol, and penicillin/streptomycin) supplemented with 20% Fibrolife serum-free cell culture medium, 20 ng/ml HGF, 1 μM A83-01, 2 μM SB43852 and 5 μM Y27632, followed by analysis at any time while subculturing the cells in Hepato-medium (plus).

HUVECs were transfected with an empty vector (mock), a combination of HNF4A and FOXA3 (H4A/F3), a combination of HNF4A, FOXA3, HNF1A and HNF6 (H4A/F3/H1A/H6), a combination of HNF4A, FOXA3 and HNF1A (H4A/F3/H1A), a combination of HNF4A, FOXA3 and HNF6 (H4A/F3/H6), a combination of HNF4A, HNF1A and HNF6 (H4A/H1A/H6), a combination of HNF4A, HNF1A, HNF6, ATFS, PROX1 and CEBPA (H4A/H1A/H6+APC) or a combination of FOXA3, HNF1A and HNF6 (F3/H1A/H6), followed by immunostaining for ALBUMIN (ALB) and counting of ALB-positive cells at each passage (P) from 1 to 6. Moreover, immunostaining for E-CADHERIN (E-CAD) was also conducted at P6.

The results obtained are shown in FIG. 1B.

ALB is a marker expressed in hepatic progenitor cells and hepatocytes, while E-CAD is a marker for epithelial cells. As can be seen from immunostaining for ALB and E-CAD, the phase contrast photographs (Phase) of the cells, as well as the graphs showing the ratio of ALB-positive cells, it is indicated that hepatic progenitor-like cells having proliferation potency are induced upon introduction of F3/H1A/H6.

In FIG. 1B, PH and PN in each graph represent parental HUVEC and passage number, respectively. Two independent experiments were conducted and the respective results are shown in blue and red lines on each graph. DNA in the cells was stained with DAPI (blue). Scale bar: 50 μm.

In addition, three independent experiments were conducted to introduce the gene set F3/H1A/H6 into HUVECs to thereby induce hiHepPCs.

The results obtained are shown in FIG. 1C. This figure shows the number of cells proliferated during 16 passages of subculture of hiHepPCs obtained in the respective experiments (hiHepPC-1, hiHepPC-2, hiHepPC-3). hiHepPCs continue to proliferate, whereas HUVECs stop their proliferation in mid-course of their subculture.

Further, the results of chromosomal analysis on hiHepPCs at the 12th passage of subculture are shown in FIG. 1D. When 20 cells were analyzed, the number of chromosomes was normal in all of them.

(2) Differentiation from hiHepPCs into Hepatocyte-Like Cells

HUVEC-derived hiHepPCs were co-immunostained for ALB and α-fetoprotein (AFP) at each passage (P) from 1 to 6 to thereby calculate the AFP-positive rate among ALB-positive cells.

Figure 2:
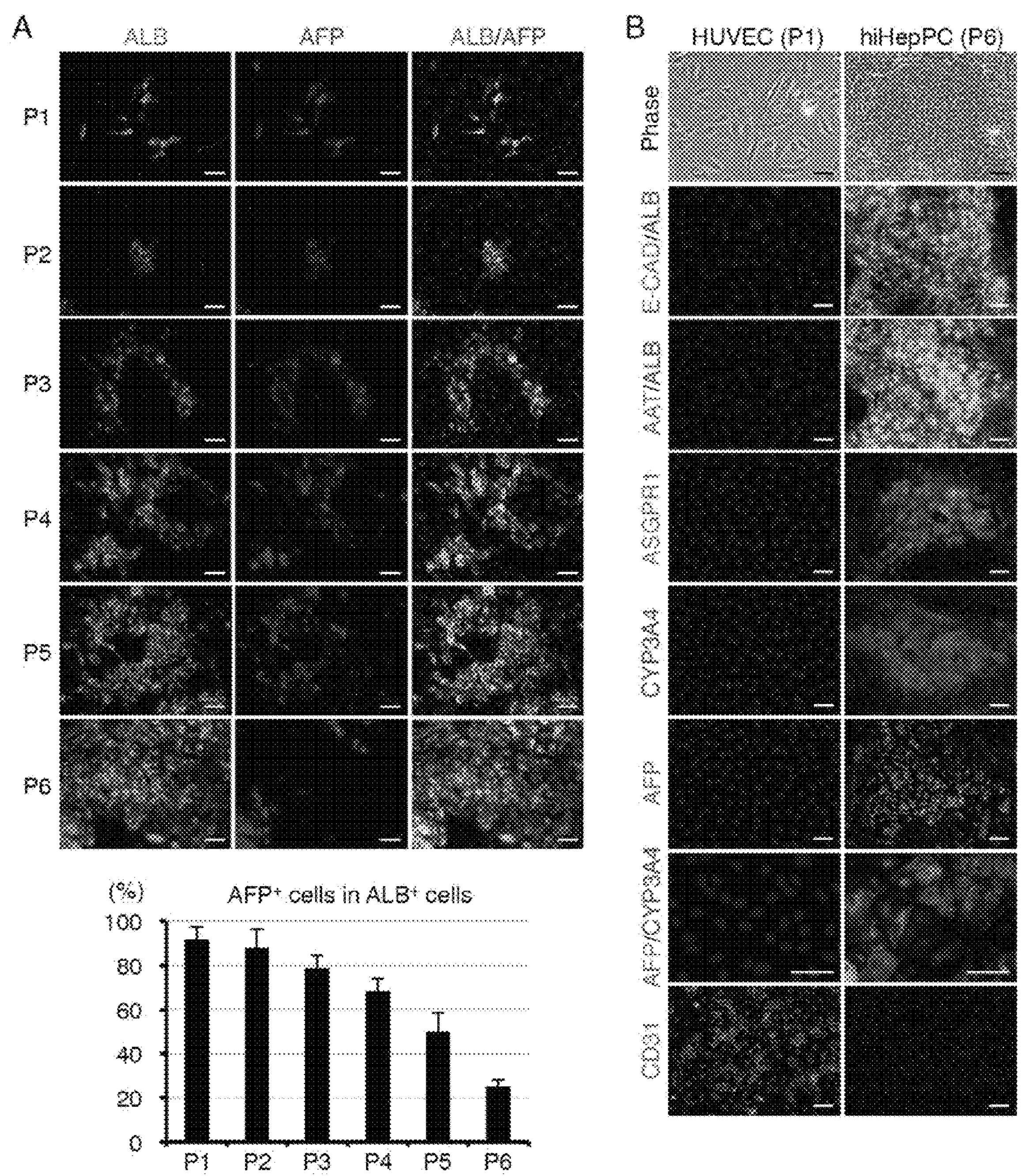
FIG. 2 shows differentiation from hiHepPCs into hepatocyte-like cells.

The results obtained are shown in FIG. 2.

In panel A, during earlier processes of hiHepPC induction, cells positive for both ALB and AFP characteristic of hepatic progenitor cells account for a higher proportion, whereas the proportion of cells positive for ALB alone characteristic of hepatocytes is increased with the number of passages. This result suggests that HUVECs will first be converted into hiHepPCs and hepatocyte-like cells will then be differentiated from hiHepPCs. The graph shows the mean±standard deviation (n=3) of data obtained by analysis on hiHepPCs prepared in three independent experiments. DNA in the cells was stained with DAPI (blue). Scale bar: 50 μm.

Likewise, as to panel B, hepatocyte-like cells differentiated from HUVEC-derived hiHepPCs express not only ALB, but also hepatocyte markers AAT, ASGPR1 and CYP3A4. On the other hand, HUVECs express a vascular endothelial cell marker, CD31, but are negative for expression of all the hepatocyte markers. DNA in the cells was stained with DAPI (blue). Scale bar: 50 μm.

Figure 3:
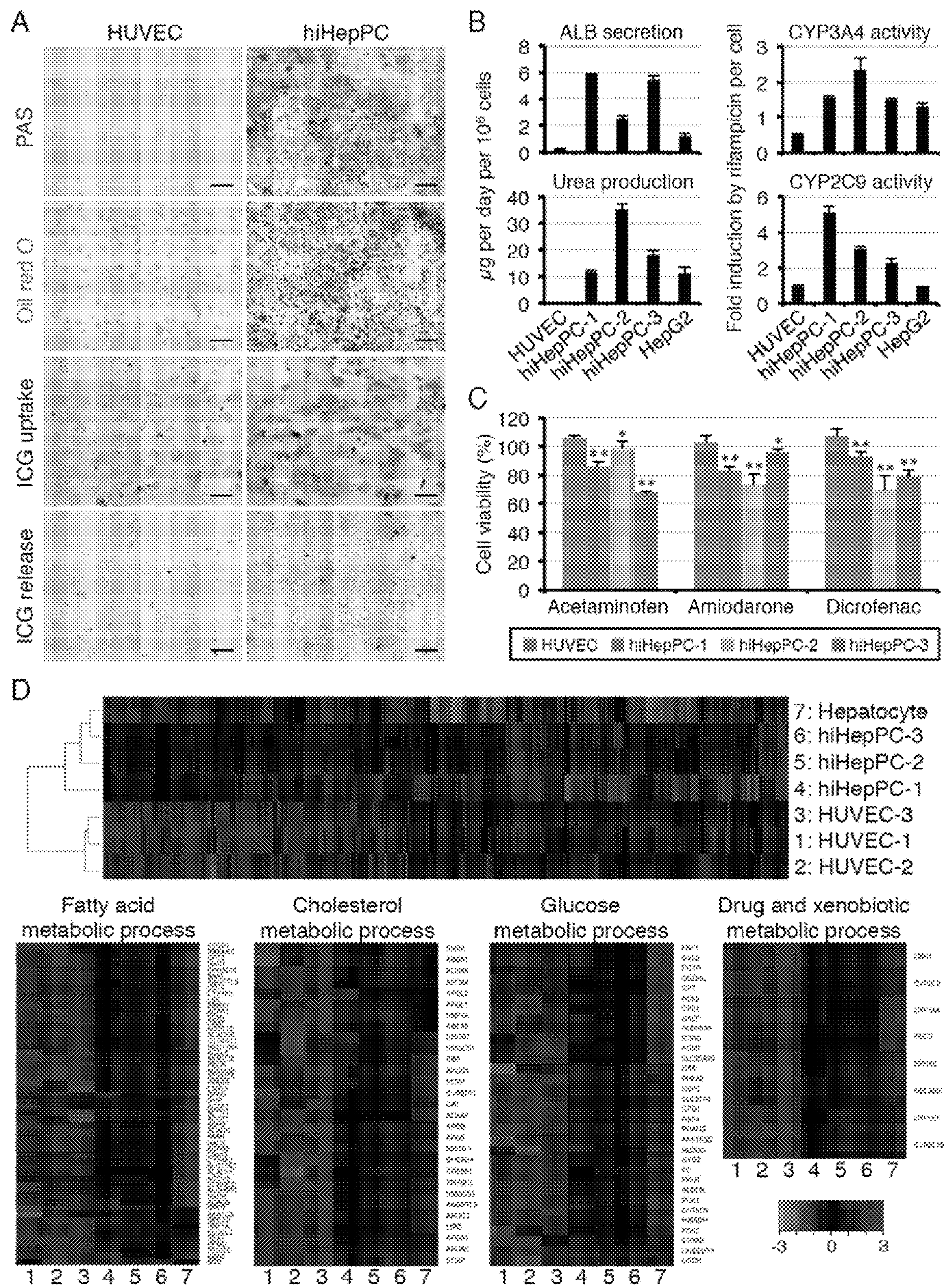
FIG. 3 shows the results of functional analysis and gene expression analysis on hepatocyte-like cells differentiated from hiHepPCs.

(3) Functional Analysis and Gene Expression Analysis on Hepatocyte-Like Cells Differentiated from hiHepPCs FIG. 3 shows the results of functional analysis and gene expression analysis on hepatocyte-like cells differentiated from hiHepPCs.

Panel A indicates that hepatocyte-like cells differentiated from HUVEC-derived hiHepPCs allow glycogen accumulation, lipid synthesis, and uptake and release of indocyanine green (ICG), as in the case of hepatocytes. Scale bar: 50 μm.

Panel B indicates that hepatocyte-like cells differentiated from HUVEC-derived hiHepPCs have the ability to cause albumin secretion, urea synthesis and cytochrome P450 activation. hiHepPCs prepared in three independent experiments (hiHepPC-1, hiHepPC-2, hiHepPC-3) were used in the analysis. A human liver cancer-derived cell line, HepG2, was used as a positive control. Each graph shows the mean±standard deviation (n=3).

Panel C indicates that hepatocyte-like cells differentiated from HUVEC-derived hiHepPCs react with hepatotoxic drugs (acetaminofen, amiodarone, dicrofenac) to cause cell death. hiHepPCs prepared in three independent experiments (hiHepPC-1, hiHepPC-2, hiHepPC-3) were used in the analysis. The graph shows the mean±standard deviation (n=3). $^{*}P<0.05$, $^{**}P<0.01$ Panel D shows the results obtained when three HUVECs (HUVEC-1, HUVEC-2, HUVEC-3) and three hiHepPCs (hiHepPC-1, hiHepPC-2, hiHepPC-3) were analyzed for their gene expression by mRNA-seq. The gene expression profile of human hepatocytes was obtained from public data, and this profile was analyzed together with the data of HUVECs and hiHepPCs. The upper heat map shows the results of clustering analysis, indicating that hiHepPCs resemble the gene expression pattern of human hepatocytes but greatly differ from HUVECs. On the other hand, the lower heat maps show the expression patterns of genes involved in fatty acid metabolism, cholesterol metabolism, glucose metabolism and drug or xenobiotic metabolism, indicating that hepatocyte-like cells differentiated from hiHepPCs express various hepatic function genes.

(4) Liver Tissue Reconstruction by hiHepPC Transplantation

First, immunodeficient mice (NSG mice) at 3 weeks of age were administered with retrorsine once a week until 7 weeks of age, i.e., five times in total. Subsequently, 1 week after the last retrorsine administration, these mice were administered once with carbon tetrachloride (CC14) to induce hepatopathy. Then, on the following day, $1\times10^{7}$ HUVEC-derived hiHepPCs were transplanted into the liver of each mouse through the portal vein from the spleen. After 2 months had passed since the transplantation, the liver and serum of each mouse were analyzed.

Figure 4:
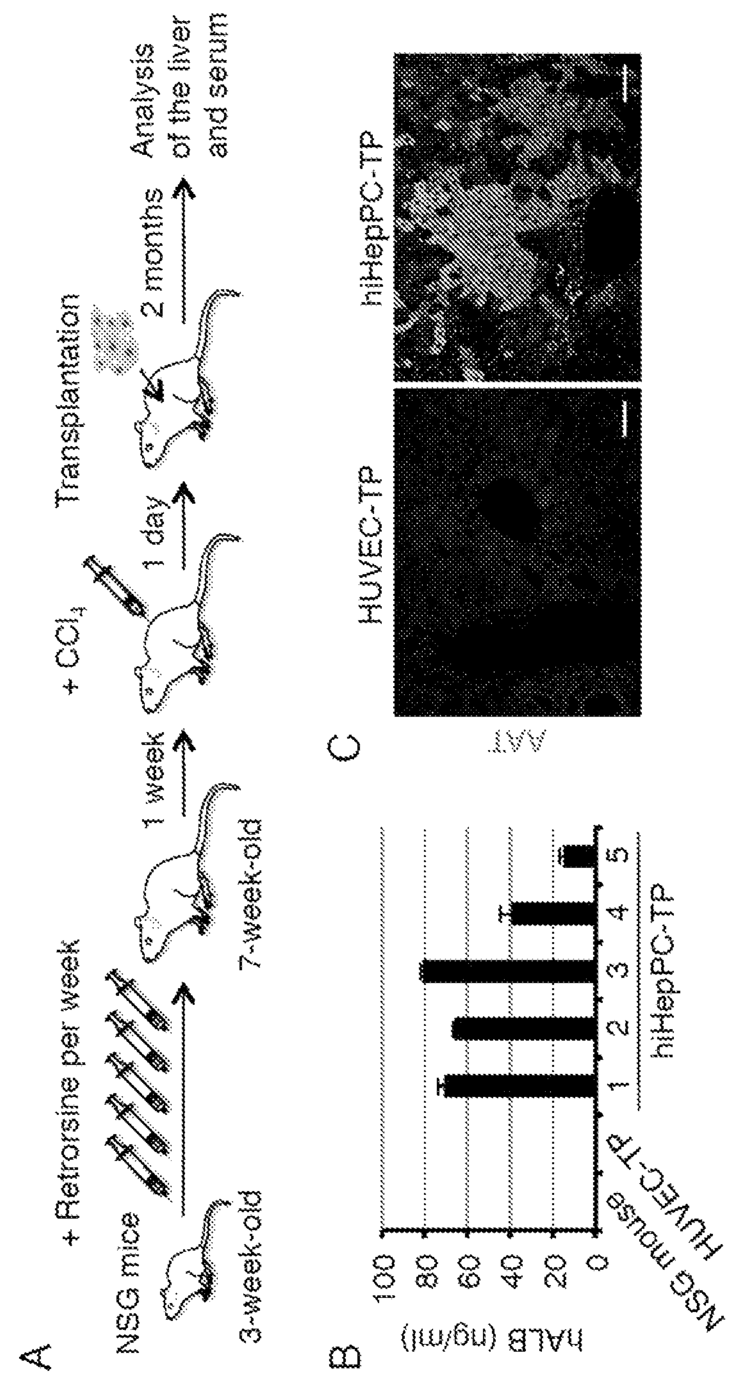
FIG. 4 shows liver tissue reconstruction by hiHepPC transplantation.

The results obtained are shown in FIG. 4.

Panel A schematically shows the hiHepPC transplantation experiment.

Panel B shows the concentration of human albumin present in mouse serum after hiHepPC transplantation. This panel shows the analysis results obtained for 5 mice transplanted with hiHepPCs. As negative controls, the analysis results obtained for non-transplanted NSG mouse serum and HUVEC-transplanted NSG mouse serum are shown. TP represents transplantation. The graph shows the mean±standard deviation (n=2).

Panel C shows the results obtained when HUVEC- or hiHepPC-transplanted mouse liver tissue was immunostained with anti-human AAT antibody. Liver tissue reconstruction by hiHepPC-derived hepatocyte-like cells is observed in the hiHepPC-transplanted mouse liver. TP represents transplantation. DNA in the cells was stained with DAPI (blue). Scale bar: 100 μm.

(5) Differentiation from hiHepPCs into Cholangiocyte-Like Cells

Figure 5:
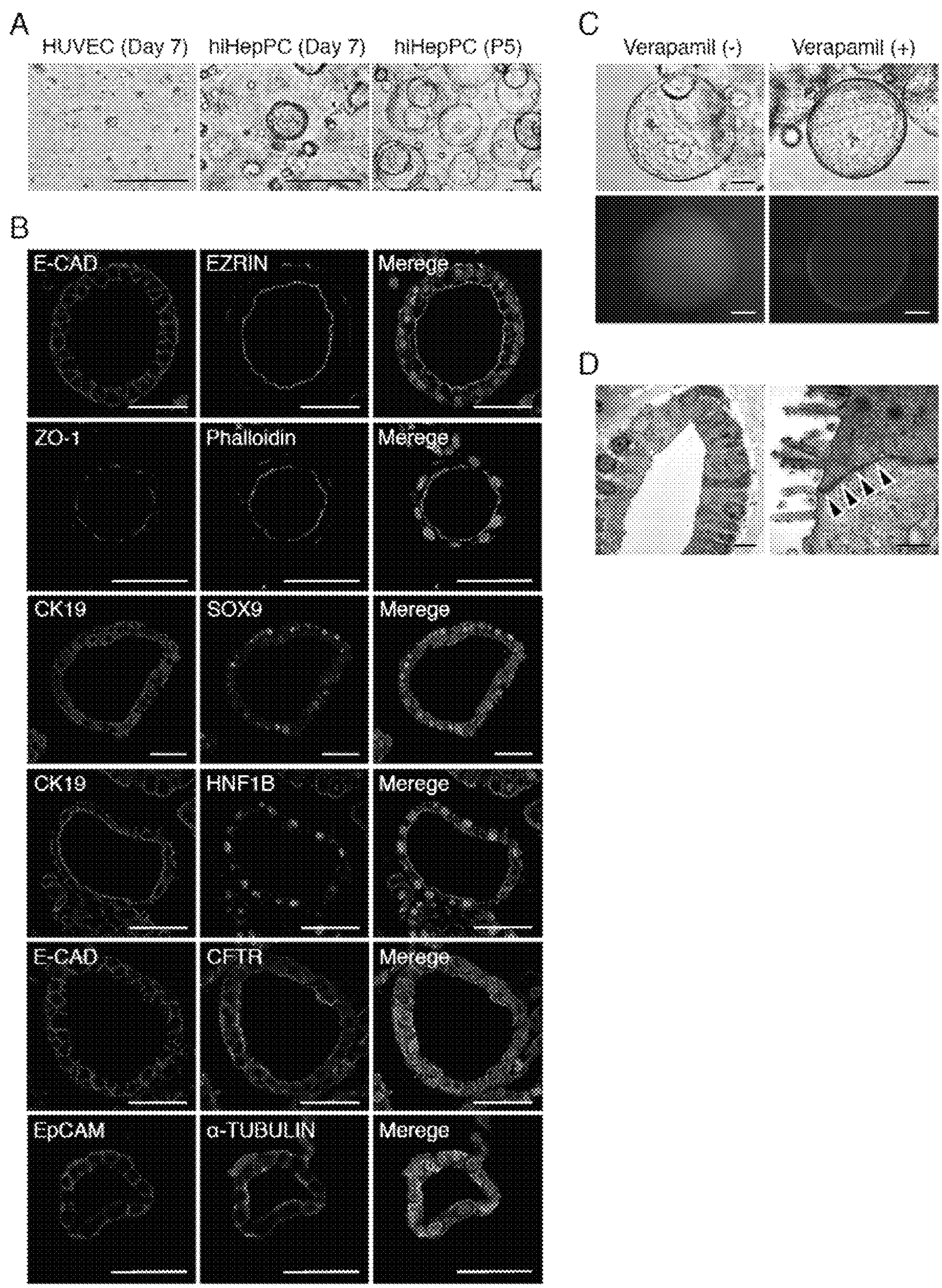
FIG. 5 shows differentiation from hiHepPCs into cholangiocyte-like cells.

FIG. 5 shows differentiation from hiHepPCs into cholangiocyte-like cells.

Panel A indicates that when HUVECs and HUVEC-derived hiHepPCs are three-dimensionally cultured in Matri gel for 1 week, only hiHepPCs form spherical tissue (spheroid) having an epithelial luminal structure. These spheroids can be subcultured for passages (P). Scale bar: 100 μm.

Panel B indicates that a spheroid formed from HUVEC-derived hiHepPCs has polarity (local expression patterns of E-CAD, EZRIN, ZO-1 and Phalloidin) and is formed by epithelial cells expressing cholangiocyte markers (CK19, SOX9, HNF1B, CFTR, EpCAM, α-TUBULIN). DNA in the cells was stained with DAPI (blue). Scale bar: 50 μm.

Panel C indicates that a spheroid formed from HUVEC-derived hiHepPCs also takes up a fluorescent dye (rhodamine), as in the case of the bile duct. The uptake is inhibited upon Verapamil addition, thus indicating that this uptake is mediated by a transporter. Scale bar: 50 μm.

Panel D shows electron microscope photographs of a spheroid formed from HUVEC-derived hiHepPCs. The spheroid has microvilli on the luminal side and its cells are joined by tight junction (indicated with arrows in the figure). Scale bar: 10 μm (left figure), 500 nm (right figure).

(6) Analysis of HUVEC-derived hiHepPCs for their proliferation potency and differentiation potency by clone analysis hiHepPCs prepared in three independent experiments (hiHepPC-1, hiHepPC-2, hiHepPC-3) were each subjected to clone sorting by flow cytometry (FACS) and seeded at one cell per well in a 96-well culture plate, followed by single cell culture. Then, cells expanded from one cell (hiHepPC clone) were analyzed.

Figure 6:
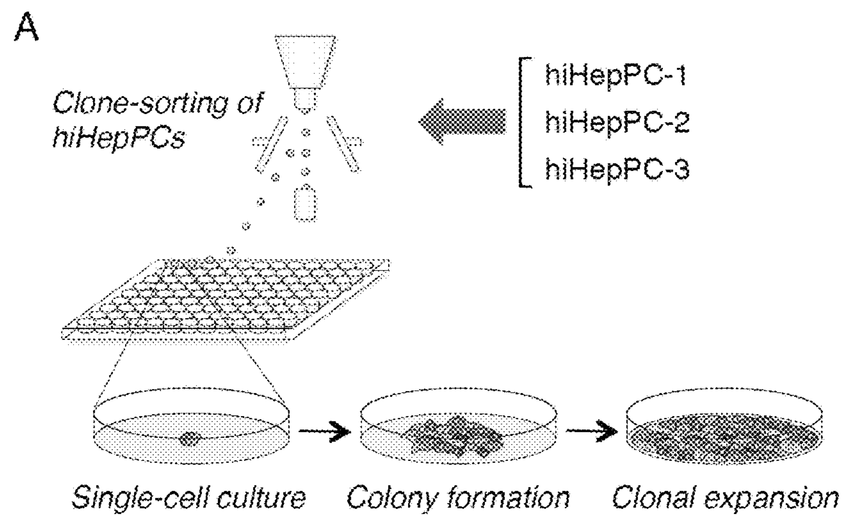
FIG. 6 shows the results obtained when HUVEC-derived hiHepPCs were analyzed for their proliferation potency and differentiation potency by clone analysis.
Figure 6:
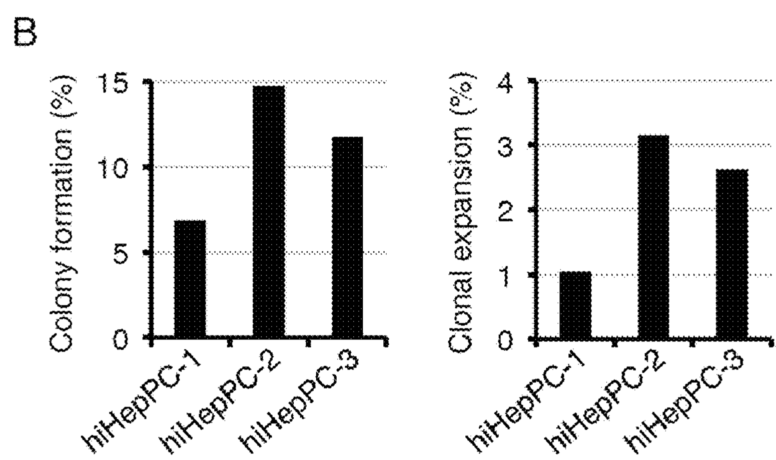
Figure 6:
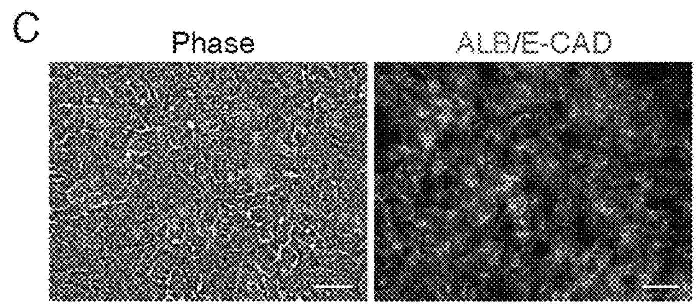
Figure 6:
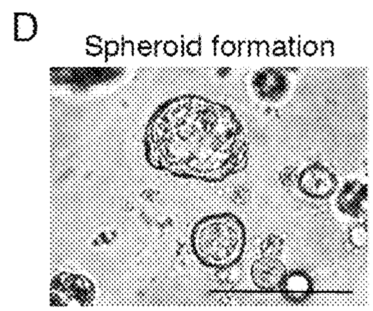

This analysis procedure is shown in FIG. 6A and the analysis results obtained are shown in FIGS. 6B to 6D.

In panel B, the graphs in the left and right figures show the ratio of colonies formed as a result of single cell culture (per 570 wells) and the ratio of clones still expanding (per 570 wells), respectively, obtained for each of hiHepPC-1, hiHepPC-2 and hiHepPC-3.

Panel C shows a phase contrast image (Phase) and an ALB and E-CAD co-immunostaining image obtained for expanded hiHepPC clones. DNA in the cells was stained with DAPI (blue). Scale bar: 50 μm. Panel D indicates that when three-dimensionally cultured in Matri gel, expanded hiHepPC clones differentiate into cholangiocyte-like cells to thereby form spheroids having an epithelial luminal structure. Scale bar: 50 μm.

(7) Reduction of the Time Required for hiHepPC Induction Upon Addition of L-MYC

In addition to FOXA3, HNF1A and HNF6, L-MYC was also simultaneously introduced into HUVECs, followed by analysis.

Figure 7:
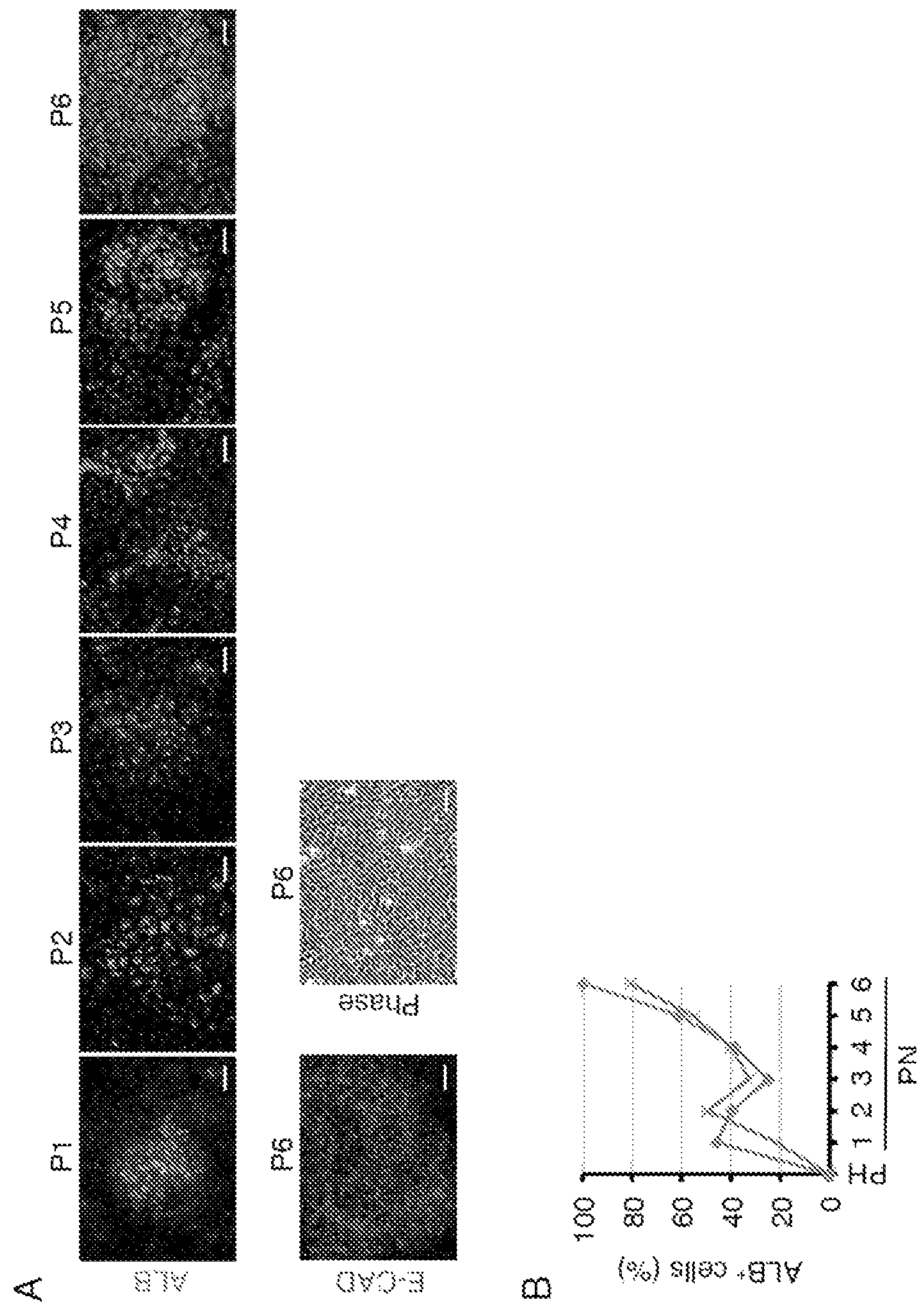
FIG. 7 shows that the time required for hiHepPC induction is reduced upon addition of L-MYC.

The results obtained are shown in FIG. 7.

In panel A, HUVECs were immunostained for ALB at each passage (P) from 1 to 6, and immunostaining for E-CAD and a phase contrast photograph (Phase) were also obtained at P6. DNA in the cells was stained with DAPI (blue). Scale bar: 50 μm.

Panel B shows the results obtained when HUVECs were transfected with a combination of F3/H1A/H6+L-MYC, followed by counting of ALB-positive cells at each passage from 1 to 6 to give the ratio of ALB-positive cells in graphical form. PH and PN in the graph represent parental HUVEC and passage number, respectively. Two independent experiments were conducted and the respective results are shown in blue and red lines on the graph. The combination of F3/H1A/H6+L-MYC was found to more quickly induce ALB-positive cells than a combination of F3/H1A/H6 (see FIG. 1B).

(8) hiHepPC Induction from Human Peripheral Blood-Derived Vascular Endothelial Cells (HPBECs)

Figure 8:
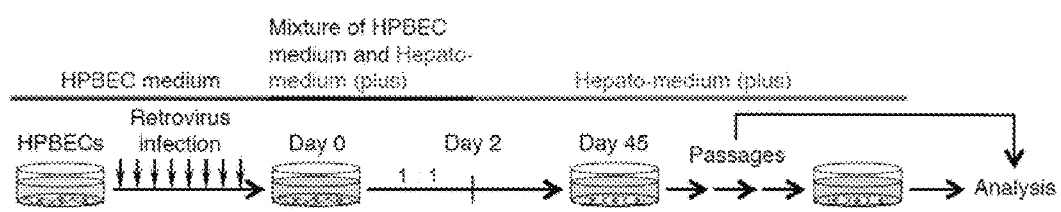
FIG. 8 shows hiHepPC induction from human peripheral blood-derived vascular endothelial cells (HPBECs).
Figure 8:
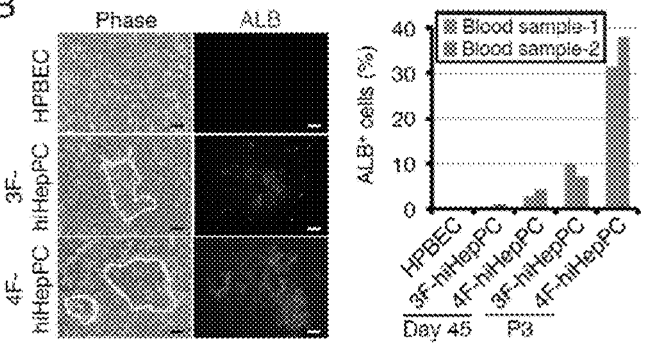
Figure 8:
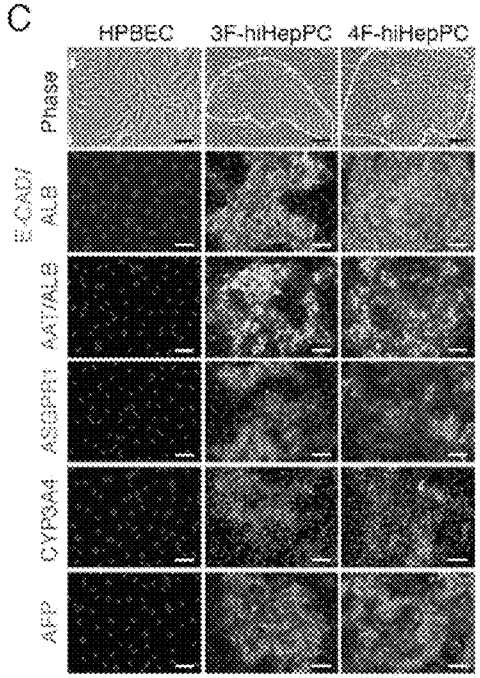
Figure 8:
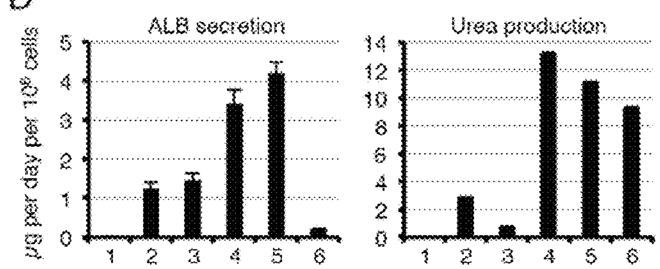
Figure 8:
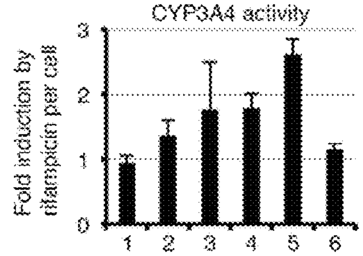
Figure 8:
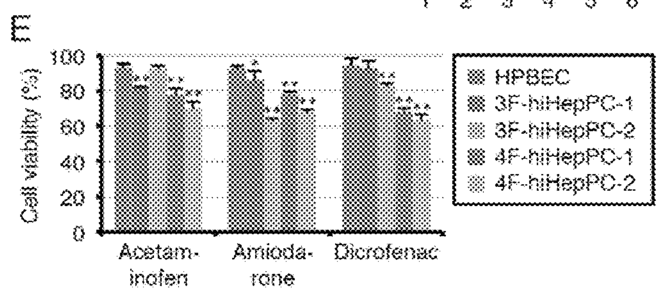
Figure 8:
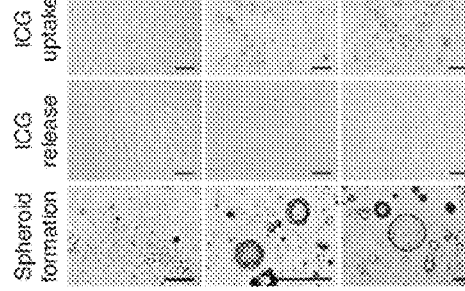

FIG. 8A schematically shows the induction experiment of hiHepPCs from HPBECs. First, mononuclear cells were separated from peripheral blood collected from normal volunteers, and were then cultured in HPBEC medium (EGM™-2MV BulletKit™ Medium supplemented with 20% fetal bovine serum) to obtain HPBECs. Then, HPBECs were transfected with a combination of F3/H1A/H6 (3F) or a combination of F3/H1A/H6+L-MYC (4F) through retrovirus infection. After virus infection, the cells were cultured for 2 days in a 1:1 mixed medium of HPBEC medium and Hepato-medium (plus). Subsequently, the cells were further cultured for 43 days in Hepato-medium (plus), followed by analysis at any time while subculturing the cells.

The results obtained are shown in FIGS. 8B to 8E.

Panel B shows phase contrast images (Phase) and ALB immunostaining images of HPBECs not receiving virus infection and HPBECs transfected with 3F or 4F (at 45 days after virus infection) (note: these photographs are not of the same field of view). A group of cells encircled with a dotted line represents induced hiHepPCs (hiHepPCs induced with 3F or 4F are expressed as 3F-hiHepPCs or 4F-hiHepPCs, respectively). The graph on the right side shows the ratio of ALB-positive cells observed among HPBECs not receiving virus infection and HPBECs transfected with 3F or 4F (at 45 days after virus infection and at the third passage (P)). Using peripheral blood collected from two normal subjects, independent experiments were conducted and the respective results are shown in blue and red bars on the graph. Scale bar: 100 μm.

Panel C indicates that 3F-hiHepPCs and 4F-hiHepPCs induced from HPBECs are both partially AFP-positive, whereas hepatocyte-like cells differentiated from 3F-hiHepPCs and 4F-hiHepPCs express not only ALB, but also hepatocyte markers AAT, ASGPR1 and CYP3A4. Moreover, hepatocyte-like cells differentiated from 3F-hiHepPCs and 4F-hiHepPCs allow glycogen accumulation, lipid synthesis, and uptake and release of indocyanine green (ICG), as in the case of hepatocytes. Furthermore, when three-dimensionally cultured in Matri gel, 3F-hiHepPCs and 4F-hiHepPCs differentiate into cholangiocyte-like cells to thereby form spheroids having an epithelial luminal structure. DNA in the cells was stained with DAPI (blue). Scale bar: 50 μm.

Panel D indicates that hepatocyte-like cells differentiated from 3F-hiHepPCs and 4F-hiHepPCs have the ability to cause albumin secretion, urea synthesis and cytochrome P450 activation. 3F-hiHepPCs (3F-hiHepPC-1, 3F-hiHepPC-2) and 4F-hiHepPCs (4F-hiHepPC-1, 4F-hiHepPC-2) prepared using peripheral blood from two normal subjects were used in the analysis. A human liver cancer-derived cell line, HepG2, was used as a positive control. Each graph shows the mean±standard deviation (n=3).

Panel E indicates that hepatocyte-like cells differentiated from 3F-hiHepPCs and 4F-hiHepPCs react with hepatotoxic drugs (acetaminofen, amiodarone, dicrofenac) to cause cell death. 3F-hiHepPCs (3F-hiHepPC-1, 3F-hiHepPC-2) and 4F-hiHepPCs (4F-hiHepPC-1, 4F-hiHepPC-2) prepared using peripheral blood from two normal subjects were used in the analysis. The graph shows the mean±standard deviation (n=3). *P<0.05, **P<0.01

Figure 9:
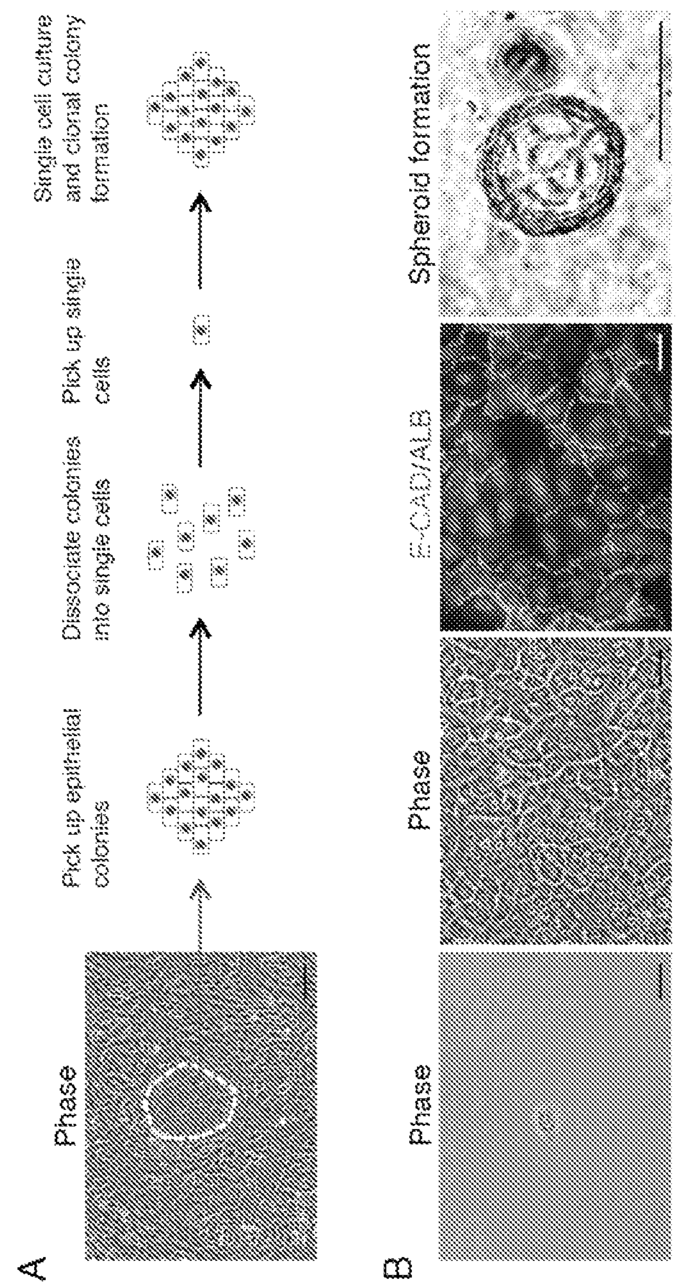
FIG. 9 shows the results obtained when HPBEC-derived 4F-hiHepPCs were analyzed for their proliferation potency and differentiation potency by clone analysis.

(9) Analysis of HPBEC-Derived 4F-hiHepPCs for their Proliferation Potency and Differentiation Potency by Clone Analysis Procedures for clone analysis of the cells and the results obtained are shown in FIG. 9.

In panel A, a colony of HPBEC-derived 4F-hiHepPCs encircled with a dotted line was picked up, and the cells were dissociated and then seeded at one cell per well in a 96-well culture plate, followed by single cell culture. Then, cells expanded from one cell (4F-hiHepPC clone) were analyzed. Scale bar: 100 μm.

Panel B shows, from the left side, a phase contrast image (Phase) of one cell (4F-hiHepPC clone) seeded in one well of the 96-well culture plate, a phase contrast image (Phase) of cells expanded from one cell, an ALB and E-CAD co-immunostaining image of the expanded cells, and a spheroid having an epithelial luminal structure, which was formed upon three-dimensional culture of cholangiocyte-like cells differentiated from the expanded cells. DNA in the cells was stained with DAPI (blue). Scale bar: 50 μm.

(10) Experiments with FOXA1 and FOXA2

Figure 10:
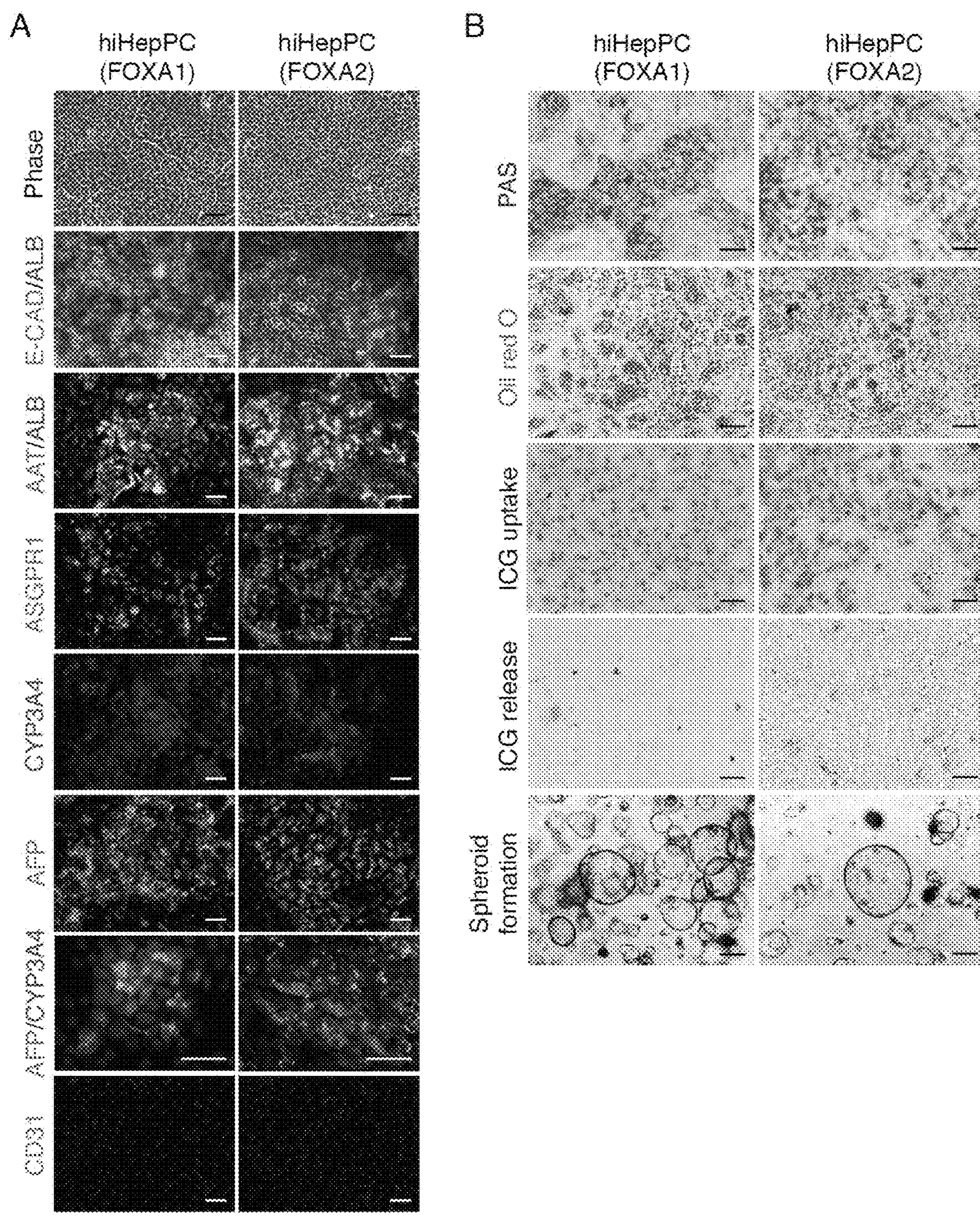
FIG. 10 shows the analysis results obtained when FOXA3, which is one of the hiHepPC-inducing factors, was replaced with FOXA1 and FOXA2.

FIG. 10 indicates that FOXA3, which is one of the hiHepPC-inducing factors, can be replaced with FOXA1 or FOXA2.

Panel A indicates that hiHepPCs (FOXA1) induced from HUVECs with a combination of FOXA1, HNF1A and HNF6 as well as hiHepPCs (FOXA2) induced from HUVECs with a combination of FOXA2, HNF1A and HNF6 both have epithelial cell morphology, do not express a vascular endothelial cell marker, CD31, and are partially AFP-positive, as in the case of hiHepPCs induced with a combination of FOXA3, HNF1A and HNF6. On the other hand, hepatocyte-like cells differentiated from hiHepPCs (FOXA1) and hiHepPCs (FOXA2) express not only ALB, but also hepatocyte markers AAT, ASGPR1 and CYP3A4. DNA in the cells was stained with DAPI (blue). Scale bar: 50 μm.

Panel B indicates that hepatocyte-like cells differentiated from HUVEC-derived hiHepPCs (FOXA1) and hiHepPCs (FOXA2) allow glycogen accumulation, lipid synthesis, and uptake and release of indocyanine green (ICG), as in the case of hepatocytes. Furthermore, when three-dimensionally cultured in Matri gel, hiHepPCs (FOXA1) and hiHepPCs (FOXA2) differentiate into cholangiocyte-like cells to thereby form spheroids having an epithelial luminal structure. Scale bar: 50 μm.

(11) hiHepPC Induction from Human Peripheral Blood-Derived T Cells (HPBTCs)

Mononuclear cells were separated from human peripheral blood and then cultured in T cell medium (a 1:1 mixed medium of HPBEC medium and Fibrolife serum-free cell culture medium supplemented with 10 ng/ml rIL-2 and 0.05 pl/cell Dynabeads HumanT-Activator CD3/CD28) to facilitate T cell expansion.

Figure 11:
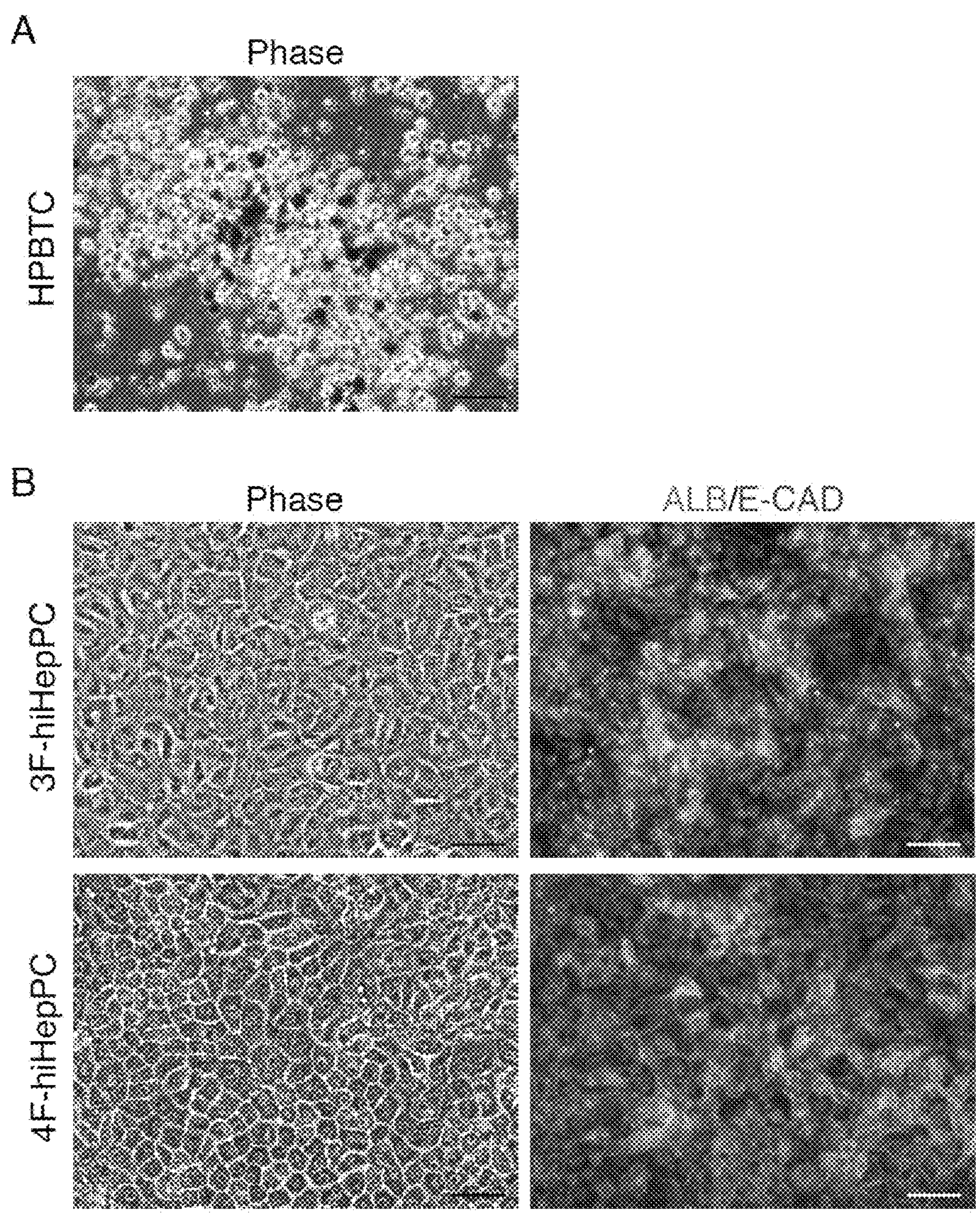
FIG. 11 shows hiHepPC induction from human peripheral blood-derived T cells (HPBTCs).

The results obtained are shown in FIG. 11.

The photograph in panel A shows a phase contrast image (Phase) of HPBTCs before hiHepPC induction. Scale bar: 50 μm.

Panel B shows phase contrast images (Phase) and ALB and E-CAD co-immunostaining images of 3F-hiHepPCs and 4F-hiHepPCs prepared from HPBTCs by transfection with a combination of F3/H1A/H6 (3F) or a combination of F3/H1A/H6+L-MYC (4F). DNA in the cells was stained with DAPI (blue). Scale bar: 50 μm.

Figure 12:
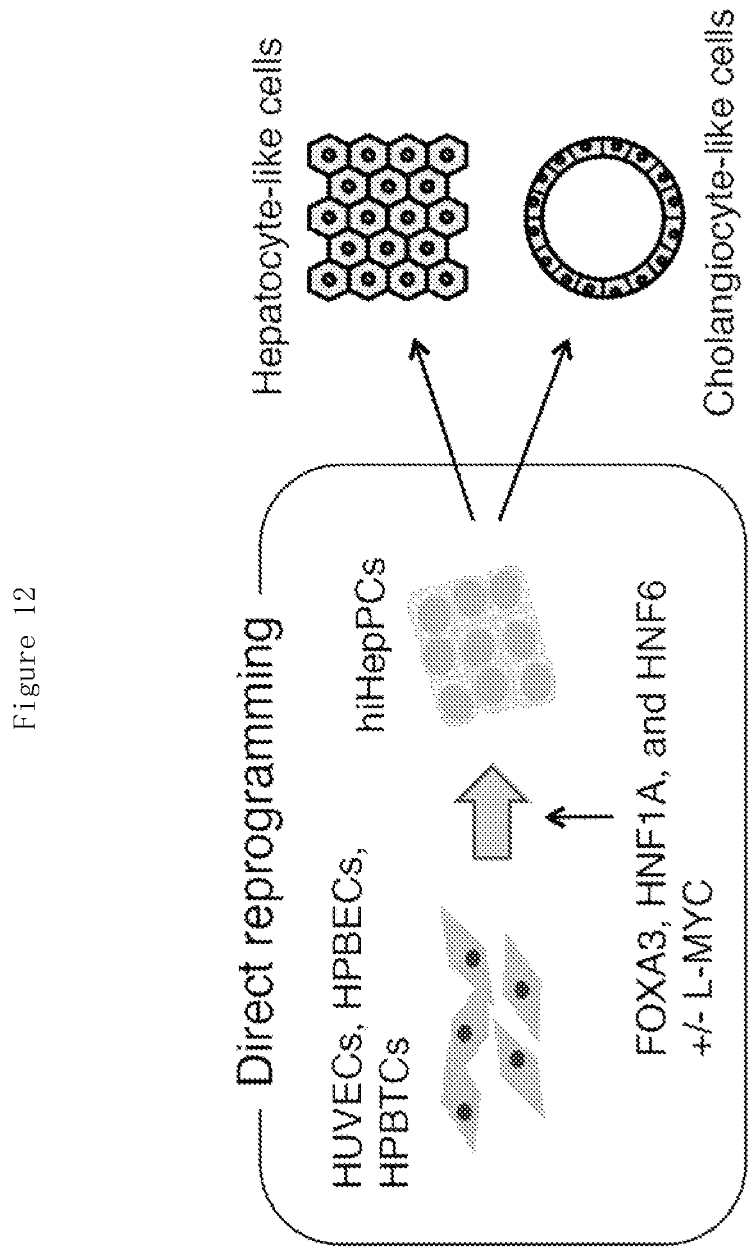
FIG. 12 shows an overview of the present invention.

The foregoing experiments indicate that when introduced into HUVECs, HPBECs or HPBTCs, a combination of FOXA3, HNF1A and HNF6 (optionally together with L-MYC) allows induction (direct reprogramming) of hiHepPCs which have proliferation potency and are capable of differentiating into hepatocyte-like cells and cholangiocyte-like cells. A summary of these experiments is shown in FIG. 12.

Using the same procedure, the inventors of the present invention have also succeeded in allowing human fibroblasts to differentiate into hepatocyte-like cells and cholangiocyte-like cells. Moreover, using the same procedure, the inventors of the present invention have also succeeded in allowing human umbilical cord blood T cells to differentiate into hepatocyte-like cells and cholangiocyte-like cells.

Furthermore, the inventors of the present invention have also succeeded in allowing human umbilical cord blood T cells to differentiate into hepatocyte-like cells and cholangiocyte-like cells by introducing a combination of FOXA3, HNF1A and L-MYC into the human umbilical cord blood T cells.

Sequence Listing Free Text

SEQ ID NO: 12: Xaa represents Ser or Thr (Location: 362).

The invention claimed is:

1. An in vitro method for inducing conversion from non-hepatic stem cells or non-hepatic progenitor cells into hepatic stem cells or hepatic progenitor cells having proliferation potency, which comprises introducing any of the following combinations into the non-hepatic stem cells or non-hepatic progenitor cells:

(a) a combination consisting of (i) HNF1A, (ii) HNF6 and (iii) FOXA3; or (b) a combination consisting of (i) HNF1A gene, (ii) HNF6 gene and (iii) FOXA3 gene;

(c) a combination consisting of (i) HNF1A, (ii) HNF6, (iii) FOXA3 and (iv) L-MYC; or (d) a combination consisting of (i) HNF1A gene, (ii) HNF6 gene, (iii) FOXA3 gene and (iv) L-MYC gene.

2. A method for obtaining hepatic stem cells or hepatic progenitor cells, which comprises the steps of:

inducing hepatic stem cells or hepatic progenitor cells by the in vitro method according to claim 1; and culturing the induced hepatic stem cells or hepatic progenitor cells to obtain additional hepatic stem cells or additional progenitor cells.

3. The method according to claim 1 or 2, wherein the non-hepatic stem cells or non-hepatic progenitor cells are vascular endothelial cells or blood-derived cells.

4. The method according to claim 3, wherein the vascular endothelial cells are derived from umbilical veins, peripheral blood or umbilical cord blood.

5. The method according to claim 3, wherein the blood-derived cells are peripheral blood T cells or umbilical cord blood T cells.

6. A method for producing hepatocytes or cholangiocytes, which comprises the steps of:

(a) inducing hepatic stem cells or hepatic progenitor cells by the in vitro method according to claim 1; and (b) differentiating the induced hepatic stem cells or hepatic progenitor cells into hepatocytes or cholangiocytes.

7. The method according to claim 1, wherein the combination is (a) or (b).

8. The method according to claim 1, wherein the combination is (c) or (d).

9. The method according to claim 1, wherein the hepatic stem cells have the ability to differentiate into cholangiocytes.

10. The method according to claim 2, wherein the additional hepatic stem cells have the ability to differentiate into cholangiocytes.

* * * * *

SEQUENCE LISTING

```
<160> NUMBER OF SEQ ID NOS: 12

<210> SEQ ID NO 1
<211> LENGTH: 3417
<212> TYPE: DNA
<213> ORGANISM: Homo sapiens
<220> FEATURE:
<221> NAME/KEY: CDS
<222> LOCATION: (202)..(2097)

<400> SEQUENCE: 1

ggggccctga ttcacgggcc gctggggcca gggttggggg ttgggggtgc ccacagggct      60

tggctagtgg ggttttgggg gggcagtggg tgcaaggagt ttggtttgtg tctgccggcc     120
```

-continued

```
ggcaggcaaa cgcaacccac gcggtggggg aggcggctag cgtggtggac ccgggccgcg    180

tggccctgtg gcagccgagc c atg gtt tct aaa ctg agc cag ctg cag acg      231
                        Met Val Ser Lys Leu Ser Gln Leu Gln Thr
                        1               5                   10

gag ctc ctg gcg gcc ctg ctc gag tca ggg ctg agc aaa gag gca ctg      279
Glu Leu Leu Ala Ala Leu Leu Glu Ser Gly Leu Ser Lys Glu Ala Leu
                15                  20                  25

atc cag gca ctg ggt gag ccg ggg ccc tac ctc ctg gct gga gaa ggc      327
Ile Gln Ala Leu Gly Glu Pro Gly Pro Tyr Leu Leu Ala Gly Glu Gly
            30                  35                  40

ccc ctg gac aag ggg gag tcc tgc ggc ggc ggt cga ggg gag ctg gct      375
Pro Leu Asp Lys Gly Glu Ser Cys Gly Gly Gly Arg Gly Glu Leu Ala
        45                  50                  55

gag ctg ccc aat ggg ctg ggg gag act cgg ggc tcc gag gac gag acg      423
Glu Leu Pro Asn Gly Leu Gly Glu Thr Arg Gly Ser Glu Asp Glu Thr
    60                  65                  70

gac gac gat ggg gaa gac ttc acg cca ccc atc ctc aaa gag ctg gag      471
Asp Asp Asp Gly Glu Asp Phe Thr Pro Pro Ile Leu Lys Glu Leu Glu
75                  80                  85                  90

aac ctc agc cct gag gag gcg gcc cac cag aaa gcc gtg gtg gag acc      519
Asn Leu Ser Pro Glu Glu Ala Ala His Gln Lys Ala Val Val Glu Thr
                95                  100                 105

ctt ctg cag gag gac ccg tgg cgt gtg gcg aag atg gtc aag tcc tac      567
Leu Leu Gln Glu Asp Pro Trp Arg Val Ala Lys Met Val Lys Ser Tyr
            110                 115                 120

ctg cag cag cac aac atc cca cag cgg gag gtg gtc gat acc act ggc      615
Leu Gln Gln His Asn Ile Pro Gln Arg Glu Val Val Asp Thr Thr Gly
        125                 130                 135

ctc aac cag tcc cac ctg tcc caa cac ctc aac aag ggc act ccc atg      663
Leu Asn Gln Ser His Leu Ser Gln His Leu Asn Lys Gly Thr Pro Met
    140                 145                 150

aag acg cag aag cgg gcc gcc ctg tac acc tgg tac gtc cgc aag cag      711
Lys Thr Gln Lys Arg Ala Ala Leu Tyr Thr Trp Tyr Val Arg Lys Gln
155                 160                 165                 170

cga gag gtg gcg cag cag ttc acc cat gca ggg cag gga ggg ctg att      759
Arg Glu Val Ala Gln Gln Phe Thr His Ala Gly Gln Gly Gly Leu Ile
                175                 180                 185

gaa gag ccc aca ggt gat gag cta cca acc aag aag ggg cgg agg aac      807
Glu Glu Pro Thr Gly Asp Glu Leu Pro Thr Lys Lys Gly Arg Arg Asn
            190                 195                 200

cgt ttc aag tgg ggc cca gca tcc cag cag atc ctg ttc cag gcc tat      855
Arg Phe Lys Trp Gly Pro Ala Ser Gln Gln Ile Leu Phe Gln Ala Tyr
        205                 210                 215

gag agg cag aag aac cct agc aag gag gag cga gag acg cta gtg gag      903
Glu Arg Gln Lys Asn Pro Ser Lys Glu Glu Arg Glu Thr Leu Val Glu
    220                 225                 230

gag tgc aat agg gcg gaa tgc atc cag aga ggg gtg tcc cca tca cag      951
Glu Cys Asn Arg Ala Glu Cys Ile Gln Arg Gly Val Ser Pro Ser Gln
235                 240                 245                 250

gca cag ggg ctg ggc tcc aac ctc gtc acg gag gtg cgt gtc tac aac      999
Ala Gln Gly Leu Gly Ser Asn Leu Val Thr Glu Val Arg Val Tyr Asn
                255                 260                 265

tgg ttt gcc aac cgg cgc aaa gaa gaa gcc ttc cgg cac aag ctg gcc     1047
Trp Phe Ala Asn Arg Arg Lys Glu Glu Ala Phe Arg His Lys Leu Ala
            270                 275                 280

atg gac acg tac agc ggg ccc ccc cca ggg cca ggc ccg gga cct gcg     1095
Met Asp Thr Tyr Ser Gly Pro Pro Pro Gly Pro Gly Pro Gly Pro Ala
        285                 290                 295

ctg ccc gct cac agc tcc cct ggc ctg cct cca cct gcc ctc tcc ccc     1143
```

-continued

```
Leu Pro Ala His Ser Ser Pro Gly Leu Pro Pro Pro Ala Leu Ser Pro
    300                 305                 310

agt aag gtc cac ggt gtg cgc tat gga cag cct gcg acc agt gag act      1191
Ser Lys Val His Gly Val Arg Tyr Gly Gln Pro Ala Thr Ser Glu Thr
315                 320                 325                 330

gca gaa gta ccc tca agc agc ggc ggt ccc tta gtg aca gtg tct aca      1239
Ala Glu Val Pro Ser Ser Ser Gly Gly Pro Leu Val Thr Val Ser Thr
                335                 340                 345

ccc ctc cac caa gtg tcc ccc acg ggc ctg gag ccc agc cac agc ctg      1287
Pro Leu His Gln Val Ser Pro Thr Gly Leu Glu Pro Ser His Ser Leu
            350                 355                 360

ctg agt aca gaa gcc aag ctg gtc tca gca gct ggg ggc ccc ctc ccc      1335
Leu Ser Thr Glu Ala Lys Leu Val Ser Ala Ala Gly Gly Pro Leu Pro
        365                 370                 375

cct gtc agc acc ctg aca gca ctg cac agc ttg gag cag aca tcc cca      1383
Pro Val Ser Thr Leu Thr Ala Leu His Ser Leu Glu Gln Thr Ser Pro
    380                 385                 390

ggc ctc aac cag cag ccc cag aac ctc atc atg gcc tca ctt cct ggg      1431
Gly Leu Asn Gln Gln Pro Gln Asn Leu Ile Met Ala Ser Leu Pro Gly
395                 400                 405                 410

gtc atg acc atc ggg cct ggt gag cct gcc tcc ctg ggt cct acg ttc      1479
Val Met Thr Ile Gly Pro Gly Glu Pro Ala Ser Leu Gly Pro Thr Phe
                415                 420                 425

acc aac aca ggt gcc tcc acc ctg gtc atc ggc ctg gcc tcc acg cag      1527
Thr Asn Thr Gly Ala Ser Thr Leu Val Ile Gly Leu Ala Ser Thr Gln
            430                 435                 440

gca cag agt gtg ccg gtc atc aac agc atg ggc agc agc ctg acc acc      1575
Ala Gln Ser Val Pro Val Ile Asn Ser Met Gly Ser Ser Leu Thr Thr
        445                 450                 455

ctg cag ccc gtc cag ttc tcc cag ccg ctg cac ccc tcc tac cag cag      1623
Leu Gln Pro Val Gln Phe Ser Gln Pro Leu His Pro Ser Tyr Gln Gln
    460                 465                 470

ccg ctc atg cca cct gtg cag agc cat gtg acc cag agc ccc ttc atg      1671
Pro Leu Met Pro Pro Val Gln Ser His Val Thr Gln Ser Pro Phe Met
475                 480                 485                 490

gcc acc atg gct cag ctg cag agc ccc cac gcc ctc tac agc cac aag      1719
Ala Thr Met Ala Gln Leu Gln Ser Pro His Ala Leu Tyr Ser His Lys
                495                 500                 505

ccc gag gtg gcc cag tac acc cac acg ggc ctg ctc ccg cag act atg      1767
Pro Glu Val Ala Gln Tyr Thr His Thr Gly Leu Leu Pro Gln Thr Met
            510                 515                 520

ctc atc acc gac acc acc aac ctg agc gcc ctg gcc agc ctc acg ccc      1815
Leu Ile Thr Asp Thr Thr Asn Leu Ser Ala Leu Ala Ser Leu Thr Pro
        525                 530                 535

acc aag cag gtc ttc acc tca gac act gag gcc tcc agt gag tcc ggg      1863
Thr Lys Gln Val Phe Thr Ser Asp Thr Glu Ala Ser Ser Glu Ser Gly
    540                 545                 550

ctt cac acg ccg gca tct cag gcc acc acc ctc cac gtc ccc agc cag      1911
Leu His Thr Pro Ala Ser Gln Ala Thr Thr Leu His Val Pro Ser Gln
555                 560                 565                 570

gac cct gcc ggc atc cag cac ctg cag ccg gcc cac cgg ctc agc gcc      1959
Asp Pro Ala Gly Ile Gln His Leu Gln Pro Ala His Arg Leu Ser Ala
                575                 580                 585

agc ccc aca gtg tcc tcc agc agc ctg gtg ctg tac cag agc tca gac      2007
Ser Pro Thr Val Ser Ser Ser Ser Leu Val Leu Tyr Gln Ser Ser Asp
            590                 595                 600

tcc agc aat ggc cag agc cac ctg ctg cca tcc aac cac agc gtc atc      2055
Ser Ser Asn Gly Gln Ser His Leu Leu Pro Ser Asn His Ser Val Ile
        605                 610                 615
```

```
gag acc ttc atc tcc acc cag atg gcc tct tcc tcc cag taa          2097
Glu Thr Phe Ile Ser Thr Gln Met Ala Ser Ser Ser Gln
    620                 625                 630

ccacggcacc tgggccctgg ggcctgtact gcctgcttgg ggggtgatga gggcagcagc   2157

cagccctgcc tggaggacct gagcctgccg agcaaccgtg gcccttcctg gacagctgtg   2217

cctcgctccc cactctgctc tgatgcatca gaaagggagg gctctgaggc gccccaaccc   2277

gtggaggctg ctcggggtgc acaggagggg gtcgtggaga gctaggagca aagcctgttc   2337

atggcagatg taggagggac tgtcgctgct tcgtgggata cagtcttctt acttggaact   2397

gaagggggcg gcctatgact tgggcacccc cagcctgggc ctatggagag ccctgggacc   2457

gctacaccac tctggcagcc acacttctca ggacacaggc ctgtgtagct gtgacctgct   2517

gagctctgag aggccctgga tcagcgtggc cttgttctgt caccaatgta cccaccgggc   2577

cactccttcc tgccccaact ccttccagct agtgacccac atgccatttg tactgacccc   2637

atcacctact cacacaggca tttcctgggt ggctactctg tgccagagcc tggggctcta   2697

acgcctgagc ccagggaggc cgaagctaac agggaaggca ggcagggctc tcctggcttc   2757

ccatccccag cgattccctc tcccaggccc catgacctcc agctttcctg tatttgttcc   2817

caagagcatc atgcctctga ggccagcctg gcctcctgcc tctactggga aggctacttc   2877

ggggctggga agtcgtcctt actcctgtgg gagcctcgca acccgtgcca agtccaggtc   2937

ctggtggggc agctcctctg tctcgagcgc cctgcagacc ctgcccttgt ttggggcagg   2997

agtagctgag ctcacaaggc agcaaggccc gagcagctga gcagggccgg ggaactggcc   3057

aagctgaggt gcccaggaga agaaagaggt gaccccaggg cacaggagct acctgtgtgg   3117

acaggactaa cactcagaag cctgggggcc tggctggctg agggcagttc gcagccaccc   3177

tgaggagtct gaggtcctga gcactgccag gagggacaaa ggagcctgtg aacccaggac   3237

aagcatggtc ccacatccct gggcctgctg ctgagaacct ggccttcagt gtaccgcgtc   3297

taccctggga ttcaggaaaa ggcctggggt gacccggcac cccctgcagc ttgtagccag   3357

ccggggcgag tggcacgttt atttaacttt tagtaaagtc aaggagaaat gcggtggaaa   3417


<210> SEQ ID NO 2
<211> LENGTH: 631
<212> TYPE: PRT
<213> ORGANISM: Homo sapiens

<400> SEQUENCE: 2

Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
    50                  55                  60

Gly Glu Thr Arg Gly Ser Glu Asp Glu Thr Asp Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
            100                 105                 110

Trp Arg Val Ala Lys Met Val Lys Ser Tyr Leu Gln Gln His Asn Ile
        115                 120                 125
```

```
Pro Gln Arg Glu Val Val Asp Thr Thr Gly Leu Asn Gln Ser His Leu
    130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
    210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ala Met Asp Thr Tyr Ser Gly
        275                 280                 285

Pro Pro Pro Gly Pro Gly Pro Gly Pro Ala Leu Pro Ala His Ser Ser
    290                 295                 300

Pro Gly Leu Pro Pro Pro Ala Leu Ser Pro Ser Lys Val His Gly Val
305                 310                 315                 320

Arg Tyr Gly Gln Pro Ala Thr Ser Glu Thr Ala Glu Val Pro Ser Ser
                325                 330                 335

Ser Gly Gly Pro Leu Val Thr Val Ser Thr Pro Leu His Gln Val Ser
            340                 345                 350

Pro Thr Gly Leu Glu Pro Ser His Ser Leu Leu Ser Thr Glu Ala Lys
        355                 360                 365

Leu Val Ser Ala Ala Gly Gly Pro Leu Pro Pro Val Ser Thr Leu Thr
    370                 375                 380

Ala Leu His Ser Leu Glu Gln Thr Ser Pro Gly Leu Asn Gln Gln Pro
385                 390                 395                 400

Gln Asn Leu Ile Met Ala Ser Leu Pro Gly Val Met Thr Ile Gly Pro
                405                 410                 415

Gly Glu Pro Ala Ser Leu Gly Pro Thr Phe Thr Asn Thr Gly Ala Ser
            420                 425                 430

Thr Leu Val Ile Gly Leu Ala Ser Thr Gln Ala Gln Ser Val Pro Val
        435                 440                 445

Ile Asn Ser Met Gly Ser Ser Leu Thr Thr Leu Gln Pro Val Gln Phe
    450                 455                 460

Ser Gln Pro Leu His Pro Ser Tyr Gln Gln Pro Leu Met Pro Pro Val
465                 470                 475                 480

Gln Ser His Val Thr Gln Ser Pro Phe Met Ala Thr Met Ala Gln Leu
                485                 490                 495

Gln Ser Pro His Ala Leu Tyr Ser His Lys Pro Glu Val Ala Gln Tyr
            500                 505                 510

Thr His Thr Gly Leu Leu Pro Gln Thr Met Leu Ile Thr Asp Thr Thr
        515                 520                 525

Asn Leu Ser Ala Leu Ala Ser Leu Thr Pro Thr Lys Gln Val Phe Thr
    530                 535                 540
```

```
Ser Asp Thr Glu Ala Ser Ser Glu Ser Gly Leu His Thr Pro Ala Ser
545                 550                 555                 560

Gln Ala Thr Thr Leu His Val Pro Ser Gln Asp Pro Ala Gly Ile Gln
                565                 570                 575

His Leu Gln Pro Ala His Arg Leu Ser Ala Ser Pro Thr Val Ser Ser
            580                 585                 590

Ser Ser Leu Val Leu Tyr Gln Ser Ser Asp Ser Ser Asn Gly Gln Ser
        595                 600                 605

His Leu Leu Pro Ser Asn His Ser Val Ile Glu Thr Phe Ile Ser Thr
    610                 615                 620

Gln Met Ala Ser Ser Ser Gln
625                 630


<210> SEQ ID NO 3
<211> LENGTH: 4042
<212> TYPE: DNA
<213> ORGANISM: Homo sapiens
<220> FEATURE:
<221> NAME/KEY: CDS
<222> LOCATION: (129)..(1526)

<400> SEQUENCE: 3

ccccacagtg agaggaagga aggcaacagt cgccagcagc cgatgtgaag accggactcc      60

gtgcgcccct cgccgcctct gcctggccac atcgatgttg tgtccgccgc ctgctcgccc     120

ggatcacg atg aac gcg cag ctg acc atg gaa gcg atc ggc gag ctg cac      170
         Met Asn Ala Gln Leu Thr Met Glu Ala Ile Gly Glu Leu His
         1               5                   10

ggg gtg agc cat gag ccg gtg ccc gcc cct gcc gac ctg ctg ggc ggc      218
Gly Val Ser His Glu Pro Val Pro Ala Pro Ala Asp Leu Leu Gly Gly
15                  20                  25                  30

agc ccc cac gcg cgc agc tcc gtg gcg cac cgc ggc agc cac ctg ccc      266
Ser Pro His Ala Arg Ser Ser Val Ala His Arg Gly Ser His Leu Pro
                35                  40                  45

ccc gcg cac ccg cgc tcc atg ggc atg gcg tcc ctg ctg gac ggc ggc      314
Pro Ala His Pro Arg Ser Met Gly Met Ala Ser Leu Leu Asp Gly Gly
            50                  55                  60

agc ggc ggc gga gat tac cac cac cac cac cgg gcc cct gag cac agc      362
Ser Gly Gly Gly Asp Tyr His His His His Arg Ala Pro Glu His Ser
        65                  70                  75

ctg gcc ggc ccc ctg cat ccc acc atg acc atg gcc tgc gag act ccc      410
Leu Ala Gly Pro Leu His Pro Thr Met Thr Met Ala Cys Glu Thr Pro
    80                  85                  90

cca ggt atg agc atg ccc acc acc tac acc acc ttg acc cct ctg cag      458
Pro Gly Met Ser Met Pro Thr Thr Tyr Thr Thr Leu Thr Pro Leu Gln
95                  100                 105                 110

ccg ctg cct ccc atc tcc aca gtc tcg gac aag ttc ccc cac cat cac      506
Pro Leu Pro Pro Ile Ser Thr Val Ser Asp Lys Phe Pro His His His
                115                 120                 125

cac cac cac cat cac cac cac cac ccg cac cac cac cag cgc ctg gcg      554
His His His His His His His His Pro His His His Gln Arg Leu Ala
            130                 135                 140

ggc aac gtg agc ggt agc ttc acg ctc atg cgg gat gag cgc ggg ctg      602
Gly Asn Val Ser Gly Ser Phe Thr Leu Met Arg Asp Glu Arg Gly Leu
        145                 150                 155

gcc tcc atg aat aac ctc tat acc ccc tac cac aag gac gtg gcc ggc      650
Ala Ser Met Asn Asn Leu Tyr Thr Pro Tyr His Lys Asp Val Ala Gly
    160                 165                 170

atg ggc cag agc ctc tcg ccc ctc tcc agc tcc ggt ctg ggc agc atc      698
Met Gly Gln Ser Leu Ser Pro Leu Ser Ser Ser Gly Leu Gly Ser Ile
```

```
175                 180                 185                 190

cac aac tcc cag caa ggg ctc ccc cac tat gcc cac ccg ggg gcc gcc      746
His Asn Ser Gln Gln Gly Leu Pro His Tyr Ala His Pro Gly Ala Ala
                195                 200                 205

atg ccc acc gac aag atg ctc acc ccc aac ggc ttc gaa gcc cac cac      794
Met Pro Thr Asp Lys Met Leu Thr Pro Asn Gly Phe Glu Ala His His
            210                 215                 220

ccg gcc atg ctc ggc cgc cac ggg gag cag cac ctc acg ccc acc tcg      842
Pro Ala Met Leu Gly Arg His Gly Glu Gln His Leu Thr Pro Thr Ser
        225                 230                 235

gcc ggc atg gtg ccc atc aac ggc ctt cct ccg cac cat ccc cac gcc      890
Ala Gly Met Val Pro Ile Asn Gly Leu Pro Pro His His Pro His Ala
    240                 245                 250

cac ctg aac gcc cag ggc cac ggg caa ctc ctg ggc aca gcc cgg gag      938
His Leu Asn Ala Gln Gly His Gly Gln Leu Leu Gly Thr Ala Arg Glu
255                 260                 265                 270

ccc aac cct tcg gtg acc ggc gcg cag gtc agc aat gga agt aat tca      986
Pro Asn Pro Ser Val Thr Gly Ala Gln Val Ser Asn Gly Ser Asn Ser
                275                 280                 285

ggg cag atg gaa gag atc aat acc aaa gag gtg gcg cag cgt atc acc     1034
Gly Gln Met Glu Glu Ile Asn Thr Lys Glu Val Ala Gln Arg Ile Thr
            290                 295                 300

acc gag ctc aag cgc tac agc atc cca cag gcc atc ttc gcg cag agg     1082
Thr Glu Leu Lys Arg Tyr Ser Ile Pro Gln Ala Ile Phe Ala Gln Arg
        305                 310                 315

gtg ctc tgc cgc tcc cag ggg acc ctc tcg gac ctg ctg cgc aac ccc     1130
Val Leu Cys Arg Ser Gln Gly Thr Leu Ser Asp Leu Leu Arg Asn Pro
    320                 325                 330

aaa ccc tgg agc aaa ctc aaa tcc ggc cgg gag acc ttc cgg agg atg     1178
Lys Pro Trp Ser Lys Leu Lys Ser Gly Arg Glu Thr Phe Arg Arg Met
335                 340                 345                 350

tgg aag tgg ctg cag gag ccg gag ttc cag cgc atg tcc gcg ctc cgc     1226
Trp Lys Trp Leu Gln Glu Pro Glu Phe Gln Arg Met Ser Ala Leu Arg
                355                 360                 365

tta gca gca tgc aaa agg aaa gaa caa gaa cat ggg aag gat aga ggc     1274
Leu Ala Ala Cys Lys Arg Lys Glu Gln Glu His Gly Lys Asp Arg Gly
            370                 375                 380

aac aca ccc aaa aag ccc agg ttg gtc ttc aca gat gtc cag cgt cga     1322
Asn Thr Pro Lys Lys Pro Arg Leu Val Phe Thr Asp Val Gln Arg Arg
        385                 390                 395

act cta cat gca ata ttc aag gaa aat aag cgt cca tcc aaa gaa ttg     1370
Thr Leu His Ala Ile Phe Lys Glu Asn Lys Arg Pro Ser Lys Glu Leu
    400                 405                 410

caa atc acc att tcc cag cag ctg ggg ttg gag ctg agc act gtc agc     1418
Gln Ile Thr Ile Ser Gln Gln Leu Gly Leu Glu Leu Ser Thr Val Ser
415                 420                 425                 430

aac ttc ttc atg aac gca aga agg agg agt ctg gac aag tgg cag gac     1466
Asn Phe Phe Met Asn Ala Arg Arg Arg Ser Leu Asp Lys Trp Gln Asp
                435                 440                 445

gag ggc agc tcc aat tca ggc aac tca tct tct tca tca agc act tgt     1514
Glu Gly Ser Ser Asn Ser Gly Asn Ser Ser Ser Ser Ser Ser Thr Cys
            450                 455                 460

acc aaa gca tga aggaagaacc acaaactaaa acctcggtgg aaaagcttta         1566
Thr Lys Ala
        465

aattaaaaaa aatttttaaa agaccaggac ctcaagatag caggtttata cttagaaata   1626

tttgaagaaa aaaaagcgtt atttatagtc caaagaaacc aaagacttag ctcacctgca   1686

ttctgacttt gtttggagac acacacttca gcagggcggc gacttggcaa gacaaatgat   1746
```

-continued

```
gagcaggaaa acaccactgg atctcacacc ttcaatccat gaccatcctc gctgtgcttg   1806
gctgtttagt ggtttggagc atagtgattt tgagccattg agcggacatc ttttaagatc   1866
gaactttctc atctgttcta ccatgccacg aaggtgtatg gtgtctcagt actaccacca   1926
ccagtggtta cagacttagg cagagctggt cttcagaaat ggttgttcta taggagtgca   1986
accaacatgg tatggggttg tctgagttca ttggattagg agtgtgattt tgctcgtcta   2046
gcctaacgtt tgaacctgcc aggcccgcaa cctaaatgca gattcaaacc cagcaaagaa   2106
aatttgaatg acacctaaac cagtgcattc tctttgtttg ttaaggaatg ttcagatatt   2166
ttttaagaaa tgaaacatga gtccatccat taaaaaaatc acctaggtac caaagaacac   2226
acttaatatt atagtgcagg tattttattg caatgatttt aataaccaaa gctattttta   2286
cacaagatac tatgaaaagt tatacgtatg aactgatcta gctgtaatac acatgccaca   2346
tagaatcatg actattattt atgactcttg aagcatttga aatatgagtt ttcagaactg   2406
gcaagaaaga atgtagcttc agggaagcaa ttaatatcat ggcagagagg tcgatgcagt   2466
acacgtgtac atccagatgg cacactcctt ttcaggatcc ataaatgtca cttaagtaga   2526
gagatagaca tggttccata atctgttcct agctgagaaa acctgaggat ctttccaaag   2586
tagtacccca tttttacact agaaaactaa atttaacagg gagggtaact aaattagaaa   2646
atttgttcaa agtaatgctt tttagtaaaa ggtcactaaa taaagaacta tccttagatt   2706
aattgactta tatttgcttt atgcatctgg caccaaaaac ctcttttaaa tactttacaa   2766
atacaaataa agtttaaaaa aacaacatta ttattcaaat gagctattca gtacttataa   2826
ctatcctaaa aagttatcaa attaacttat tgccaatccc agaaatttta tgacttggac   2886
gtcaacaaaa cagcaggtgc aactgagaaa tggtggaatt ggtggaactg tatagaaaaa   2946
agccagtgtt ctggtggacg acaagacttt tgatctattg gtattaatca atttatggaa   3006
ctaagaatag cctccaaagc attctgcctt ctttcttgct actgcattta gctggaaatt   3066
ttataatata gattttgctc tctaacaggg acagattaaa aactagacct gagcttacaa   3126
atacaaaatt ttaaatttct atttgtccaa atcacttaac cagagctgta gaagtcaaag   3186
tcaaaaaaaa aatgaagtcg tattagtggt accccagtga atcacttgat tcccagaaaa   3246
attctctctg aattcagttg gactgtaact tatctaagtg gatgcccctt atgccattag   3306
gtaaagaatt ggatactgta agttaattac cacccctact tagaactatg aaattaaatg   3366
ttatcctaat gataagttgt tttattgaga ttcattaaaa atgccaaaga acaaaactga   3426
accatcttga cacaaaacat aactccttag catcaaatct cagcaccttg tctaggtctg   3486
taacaggcag gcaactagag aggtaaagca aaaccaacaa gccatctatc tgtgtctcct   3546
tcatgtctgc tgtcgaatga gaagaggaaa ccaacatata cttctctttt gatgaaatac   3606
ttcatttgcc ttgacatgtt ttgtttttttg tttttaattt cacccacaac tccagcttaa   3666
aaatttccct tctaaatatg gcacaattat agttcagcta ttgaaagaga ccatttaaat   3726
ggccaccctt caagatttac taaaaaatag aatcttgtca atgacataaa caaaaaggaa   3786
aaaactgatt aacattttct ctctctccag ggatggaggg agccggggat acagctacat   3846
aatgtattta taatttagga gggaggaaag ccttatttat ttaaaacgtg ataattctaa   3906
atgcagggaa attcaagctg tgtctacaca caatcttacc aaattcaata ccccaagaaa   3966
agaatagcag aattcagaca accatgtttt ttatttgttg ctagtatata ttacccccaa   4026
aaaaaaaaaa aaaaaa                                                   4042
```

```
<210> SEQ ID NO 4
<211> LENGTH: 465
<212> TYPE: PRT
<213> ORGANISM: Homo sapiens

<400> SEQUENCE: 4

Met Asn Ala Gln Leu Thr Met Glu Ala Ile Gly Glu Leu His Gly Val
1               5                   10                  15

Ser His Glu Pro Val Pro Ala Pro Ala Asp Leu Leu Gly Gly Ser Pro
            20                  25                  30

His Ala Arg Ser Ser Val Ala His Arg Gly Ser His Leu Pro Pro Ala
        35                  40                  45

His Pro Arg Ser Met Gly Met Ala Ser Leu Leu Asp Gly Gly Ser Gly
    50                  55                  60

Gly Gly Asp Tyr His His His His Arg Ala Pro Glu His Ser Leu Ala
65                  70                  75                  80

Gly Pro Leu His Pro Thr Met Thr Met Ala Cys Glu Thr Pro Pro Gly
                85                  90                  95

Met Ser Met Pro Thr Thr Tyr Thr Thr Leu Thr Pro Leu Gln Pro Leu
            100                 105                 110

Pro Pro Ile Ser Thr Val Ser Asp Lys Phe Pro His His His His His
        115                 120                 125

His His His His His His Pro His His His Gln Arg Leu Ala Gly Asn
    130                 135                 140

Val Ser Gly Ser Phe Thr Leu Met Arg Asp Glu Arg Gly Leu Ala Ser
145                 150                 155                 160

Met Asn Asn Leu Tyr Thr Pro Tyr His Lys Asp Val Ala Gly Met Gly
                165                 170                 175

Gln Ser Leu Ser Pro Leu Ser Ser Ser Gly Leu Gly Ser Ile His Asn
            180                 185                 190

Ser Gln Gln Gly Leu Pro His Tyr Ala His Pro Gly Ala Ala Met Pro
        195                 200                 205

Thr Asp Lys Met Leu Thr Pro Asn Gly Phe Glu Ala His His Pro Ala
    210                 215                 220

Met Leu Gly Arg His Gly Glu Gln His Leu Thr Pro Thr Ser Ala Gly
225                 230                 235                 240

Met Val Pro Ile Asn Gly Leu Pro Pro His His Pro His Ala His Leu
                245                 250                 255

Asn Ala Gln Gly His Gly Gln Leu Leu Gly Thr Ala Arg Glu Pro Asn
            260                 265                 270

Pro Ser Val Thr Gly Ala Gln Val Ser Asn Gly Ser Asn Ser Gly Gln
        275                 280                 285

Met Glu Glu Ile Asn Thr Lys Glu Val Ala Gln Arg Ile Thr Thr Glu
    290                 295                 300

Leu Lys Arg Tyr Ser Ile Pro Gln Ala Ile Phe Ala Gln Arg Val Leu
305                 310                 315                 320

Cys Arg Ser Gln Gly Thr Leu Ser Asp Leu Leu Arg Asn Pro Lys Pro
                325                 330                 335

Trp Ser Lys Leu Lys Ser Gly Arg Glu Thr Phe Arg Arg Met Trp Lys
            340                 345                 350

Trp Leu Gln Glu Pro Glu Phe Gln Arg Met Ser Ala Leu Arg Leu Ala
        355                 360                 365

Ala Cys Lys Arg Lys Glu Gln Glu His Gly Lys Asp Arg Gly Asn Thr
    370                 375                 380
```

```
Pro Lys Lys Pro Arg Leu Val Phe Thr Asp Val Gln Arg Arg Thr Leu
385                 390                 395                 400

His Ala Ile Phe Lys Glu Asn Lys Arg Pro Ser Lys Glu Leu Gln Ile
                405                 410                 415

Thr Ile Ser Gln Gln Leu Gly Leu Glu Leu Ser Thr Val Ser Asn Phe
            420                 425                 430

Phe Met Asn Ala Arg Arg Arg Ser Leu Asp Lys Trp Gln Asp Glu Gly
        435                 440                 445

Ser Ser Asn Ser Gly Asn Ser Ser Ser Ser Ser Ser Thr Cys Thr Lys
    450                 455                 460

Ala
465


<210> SEQ ID NO 5
<211> LENGTH: 3396
<212> TYPE: DNA
<213> ORGANISM: Homo sapiens
<220> FEATURE:
<221> NAME/KEY: CDS
<222> LOCATION: (149)..(1567)

<400> SEQUENCE: 5

gggcttcctc ttcgcccggg tggcgttggg cccgcgcggg cgctcgggtg actgcagctg      60

ctcagctccc ctcccccgcc ccgcgccgcg cggccgcccg tcgcttcgca cagggctgga     120

tggttgtatt gggcagggtg gctccagg atg tta gga act gtg aag atg gaa        172
                               Met Leu Gly Thr Val Lys Met Glu
                               1               5

ggg cat gaa acc agc gac tgg aac agc tac tac gca gac acg cag gag       220
Gly His Glu Thr Ser Asp Trp Asn Ser Tyr Tyr Ala Asp Thr Gln Glu
    10                  15                  20

gcc tac tcc tcc gtc ccg gtc agc aac atg aac tca ggc ctg ggc tcc       268
Ala Tyr Ser Ser Val Pro Val Ser Asn Met Asn Ser Gly Leu Gly Ser
25                  30                  35                  40

atg aac tcc atg aac acc tac atg acc atg aac acc atg act acg agc       316
Met Asn Ser Met Asn Thr Tyr Met Thr Met Asn Thr Met Thr Thr Ser
                45                  50                  55

ggc aac atg acc ccg gcg tcc ttc aac atg tcc tat gcc aac ccg ggc       364
Gly Asn Met Thr Pro Ala Ser Phe Asn Met Ser Tyr Ala Asn Pro Gly
            60                  65                  70

cta ggg gcc ggc ctg agt ccc ggc gca gta gcc ggc atg ccg ggg ggc       412
Leu Gly Ala Gly Leu Ser Pro Gly Ala Val Ala Gly Met Pro Gly Gly
        75                  80                  85

tcg gcg ggc gcc atg aac agc atg act gcg gcc ggc gtg acg gcc atg       460
Ser Ala Gly Ala Met Asn Ser Met Thr Ala Ala Gly Val Thr Ala Met
    90                  95                  100

ggt acg gcg ctg agc ccg agc ggc atg ggc gcc atg ggt gcg cag cag       508
Gly Thr Ala Leu Ser Pro Ser Gly Met Gly Ala Met Gly Ala Gln Gln
105                 110                 115                 120

gcg gcc tcc atg aat ggc ctg ggc ccc tac gcg gcc gcc atg aac ccg       556
Ala Ala Ser Met Asn Gly Leu Gly Pro Tyr Ala Ala Ala Met Asn Pro
                125                 130                 135

tgc atg agc ccc atg gcg tac gcg ccg tcc aac ctg ggc cgc agc cgc       604
Cys Met Ser Pro Met Ala Tyr Ala Pro Ser Asn Leu Gly Arg Ser Arg
            140                 145                 150

gcg ggc ggc ggc ggc gac gcc aag acg ttc aag cgc agc tac ccg cac       652
Ala Gly Gly Gly Gly Asp Ala Lys Thr Phe Lys Arg Ser Tyr Pro His
        155                 160                 165

gcc aag ccg ccc tac tcg tac atc tcg ctc atc acc atg gcc atc cag       700
```

-continued

```
Ala Lys Pro Pro Tyr Ser Tyr Ile Ser Leu Ile Thr Met Ala Ile Gln
    170                 175                 180

cag gcg ccc agc aag atg ctc acg ctg agc gag atc tac cag tgg atc      748
Gln Ala Pro Ser Lys Met Leu Thr Leu Ser Glu Ile Tyr Gln Trp Ile
185                 190                 195                 200

atg gac ctc ttc ccc tat tac cgg cag aac cag cag cgc tgg cag aac      796
Met Asp Leu Phe Pro Tyr Tyr Arg Gln Asn Gln Gln Arg Trp Gln Asn
                205                 210                 215

tcc atc cgc cac tcg ctg tcc ttc aat gac tgc ttc gtc aag gtg gca      844
Ser Ile Arg His Ser Leu Ser Phe Asn Asp Cys Phe Val Lys Val Ala
            220                 225                 230

cgc tcc ccg gac aag ccg ggc aag ggc tcc tac tgg acg ctg cac ccg      892
Arg Ser Pro Asp Lys Pro Gly Lys Gly Ser Tyr Trp Thr Leu His Pro
        235                 240                 245

gac tcc ggc aac atg ttc gag aac ggc tgc tac ttg cgc cgc cag aag      940
Asp Ser Gly Asn Met Phe Glu Asn Gly Cys Tyr Leu Arg Arg Gln Lys
    250                 255                 260

cgc ttc aag tgc gag aag cag ccg ggg gcc ggc ggc ggg ggc ggg agc      988
Arg Phe Lys Cys Glu Lys Gln Pro Gly Ala Gly Gly Gly Gly Gly Ser
265                 270                 275                 280

gga agc ggg ggc agc ggc gcc aag ggc ggc cct gag agc cgc aag gac     1036
Gly Ser Gly Gly Ser Gly Ala Lys Gly Gly Pro Glu Ser Arg Lys Asp
                285                 290                 295

ccc tct ggc gcc tct aac ccc agc gcc gac tcg ccc ctc cat cgg ggt     1084
Pro Ser Gly Ala Ser Asn Pro Ser Ala Asp Ser Pro Leu His Arg Gly
            300                 305                 310

gtg cac ggg aag acc ggc cag cta gag ggc gcg ccg gcc ccc ggg ccc     1132
Val His Gly Lys Thr Gly Gln Leu Glu Gly Ala Pro Ala Pro Gly Pro
        315                 320                 325

gcc gcc agc ccc cag act ctg gac cac agt ggg gcg acg gcg aca ggg     1180
Ala Ala Ser Pro Gln Thr Leu Asp His Ser Gly Ala Thr Ala Thr Gly
    330                 335                 340

ggc gcc tcg gag ttg aag act cca gcc tcc tca act gcg ccc ccc ata     1228
Gly Ala Ser Glu Leu Lys Thr Pro Ala Ser Ser Thr Ala Pro Pro Ile
345                 350                 355                 360

agc tcc ggg ccc ggg gcg ctg gcc tct gtg ccc gcc tct cac ccg gca     1276
Ser Ser Gly Pro Gly Ala Leu Ala Ser Val Pro Ala Ser His Pro Ala
                365                 370                 375

cac ggc ttg gca ccc cac gag tcc cag ctg cac ctg aaa ggg gac ccc     1324
His Gly Leu Ala Pro His Glu Ser Gln Leu His Leu Lys Gly Asp Pro
            380                 385                 390

cac tac tcc ttc aac cac ccg ttc tcc atc aac aac ctc atg tcc tcc     1372
His Tyr Ser Phe Asn His Pro Phe Ser Ile Asn Asn Leu Met Ser Ser
        395                 400                 405

tcg gag cag cag cat aag ctg gac ttc aag gca tac gaa cag gca ctg     1420
Ser Glu Gln Gln His Lys Leu Asp Phe Lys Ala Tyr Glu Gln Ala Leu
    410                 415                 420

caa tac tcg cct tac ggc tct acg ttg ccc gcc agc ctg cct cta ggc     1468
Gln Tyr Ser Pro Tyr Gly Ser Thr Leu Pro Ala Ser Leu Pro Leu Gly
425                 430                 435                 440

agc gcc tcg gtg acc acc agg agc ccc atc gag ccc tca gcc ctg gag     1516
Ser Ala Ser Val Thr Thr Arg Ser Pro Ile Glu Pro Ser Ala Leu Glu
                445                 450                 455

ccg gcg tac tac caa ggt gtg tat tcc aga ccc gtc cta aac act tcc     1564
Pro Ala Tyr Tyr Gln Gly Val Tyr Ser Arg Pro Val Leu Asn Thr Ser
            460                 465                 470

tag ctcccgggac tggggggttt gtctggcata gccatgctgg tagcaagaga          1617

gaaaaaatca acagcaaaca aaaccacaca aaccaaaccg tcaacagcat aataaaatcc   1677
```

```
caacaactat ttttatttca tttttcatgc acaacctttc ccccagtgca aaagactgtt   1737

actttattat tgtattcaaa attcattgtg tatattacta caaagacaac cccaaaccaa   1797

tttttttcct gcgaagttta atgatccaca agtgtatata tgaaattctc ctccttcctt   1857

gccccccctct ctttcttccc tctttcccct ccagacattc tagtttgtgg agggttattt   1917

aaaaaaacaa aaaaggaaga tggtcaagtt tgtaaaatat ttgtttgtgc tttttccccc   1977

tccttacctg accccctacg agtttacagg tctgtggcaa tactcttaac cataagaatt   2037

gaaatggtga agaaacaagt atacactaga ggctcttaaa agtattgaaa gacaatactg   2097

ctgttatata gcaagacata aacagattat aaacatcaga gccatttgct tctcagttta   2157

catttctgat acatgcagat agcagatgtc tttaaatgaa atacatgtat attgtgtatg   2217

gacttaatta tgcacatgct cagatgtgta gacatcctcc gtatatttac ataacatata   2277

gaggtaatag ataggtgata tacatgatac attctcaaga gttgcttgac cgaaagttac   2337

aaggacccca accccttgt cctctctacc cacagatggc cctgggaatc aattcctcag   2397

gaattgccct caagaactct gcttcttgct ttgcagagtg ccatggtcat gtcattctga   2457

ggtcacataa cacataaaat tagtttctat gagtgtatac catttaaaga attttttttt   2517

cagtaaaagg gaatattaca atgttggagg agagataagt tatagggagc tggatttcaa   2577

aacgtggtcc aagattcaaa aatcctattg atagtggcca ttttaatcat tgccatcgtg   2637

tgcttgtttc atccagtgtt atgcactttc cacagttgga catggtgtta gtatagccag   2697

acgggtttca ttattatttc tctttgcttt ctcaatgtta atttattgca tggtttattc   2757

tttttcttta cagctgaaat tgctttaaat gatggttaaa attacaaatt aaattgttaa   2817

tttttatcaa tgtgattgta attaaaaata ttttgattta aataacaaaa ataataccag   2877

attttaagcc gtggaaaatg ttcttgatca tttgcagtta aggactttaa ataaatcaaa   2937

tgttaacaaa agagcatttc tgttattttt tttcacttaa ctaaatccga agtgaatatt   2997

tctgaatacg atatttttca aattctagaa ctgaatataa atgacaaaaa tgaaaataaa   3057

attgttttgt ctgttgttat aatgaatgtg tagctagtaa aaaggagtga aagaaattca   3117

agtaaagtgt ataagttgat ttaatattcc aagagttgag atttttaaga ttctttattc   3177

ccagtgatgt ttacttcatt tttttttttt tttttgacac cggcttaagc cttctgtgtt   3237

tcctttgagc cttttcacta caaaatcaaa tattaattta actacctttc ctccttcccc   3297

aatgtatcac ttttctttat ctgagaattc ttccaatgaa aataaaatat cagctgtggc   3357

tgatagaatt aagttgtgtc caaaaaaaaa aaaaaaaaa                          3396
```

<210> SEQ ID NO 6
<211> LENGTH: 472
<212> TYPE: PRT
<213> ORGANISM: Homo sapiens

<400> SEQUENCE: 6

```
Met Leu Gly Thr Val Lys Met Glu Gly His Glu Thr Ser Asp Trp Asn
1               5                   10                  15

Ser Tyr Tyr Ala Asp Thr Gln Glu Ala Tyr Ser Ser Val Pro Val Ser
            20                  25                  30

Asn Met Asn Ser Gly Leu Gly Ser Met Asn Ser Met Asn Thr Tyr Met
        35                  40                  45

Thr Met Asn Thr Met Thr Thr Ser Gly Asn Met Thr Pro Ala Ser Phe
    50                  55                  60

Asn Met Ser Tyr Ala Asn Pro Gly Leu Gly Ala Gly Leu Ser Pro Gly
```

-continued

```
65                  70                  75                  80

Ala Val Ala Gly Met Pro Gly Gly Ser Ala Gly Ala Met Asn Ser Met
                85                  90                  95

Thr Ala Ala Gly Val Thr Ala Met Gly Thr Ala Leu Ser Pro Ser Gly
            100                 105                 110

Met Gly Ala Met Gly Ala Gln Gln Ala Ala Ser Met Asn Gly Leu Gly
        115                 120                 125

Pro Tyr Ala Ala Ala Met Asn Pro Cys Met Ser Pro Met Ala Tyr Ala
    130                 135                 140

Pro Ser Asn Leu Gly Arg Ser Arg Ala Gly Gly Gly Gly Asp Ala Lys
145                 150                 155                 160

Thr Phe Lys Arg Ser Tyr Pro His Ala Lys Pro Pro Tyr Ser Tyr Ile
                165                 170                 175

Ser Leu Ile Thr Met Ala Ile Gln Gln Ala Pro Ser Lys Met Leu Thr
            180                 185                 190

Leu Ser Glu Ile Tyr Gln Trp Ile Met Asp Leu Phe Pro Tyr Tyr Arg
        195                 200                 205

Gln Asn Gln Gln Arg Trp Gln Asn Ser Ile Arg His Ser Leu Ser Phe
    210                 215                 220

Asn Asp Cys Phe Val Lys Val Ala Arg Ser Pro Asp Lys Pro Gly Lys
225                 230                 235                 240

Gly Ser Tyr Trp Thr Leu His Pro Asp Ser Gly Asn Met Phe Glu Asn
                245                 250                 255

Gly Cys Tyr Leu Arg Arg Gln Lys Arg Phe Lys Cys Glu Lys Gln Pro
            260                 265                 270

Gly Ala Gly Gly Gly Gly Gly Ser Gly Ser Gly Gly Ser Gly Ala Lys
        275                 280                 285

Gly Gly Pro Glu Ser Arg Lys Asp Pro Ser Gly Ala Ser Asn Pro Ser
    290                 295                 300

Ala Asp Ser Pro Leu His Arg Gly Val His Gly Lys Thr Gly Gln Leu
305                 310                 315                 320

Glu Gly Ala Pro Ala Pro Gly Pro Ala Ala Ser Pro Gln Thr Leu Asp
                325                 330                 335

His Ser Gly Ala Thr Ala Thr Gly Gly Ala Ser Glu Leu Lys Thr Pro
            340                 345                 350

Ala Ser Ser Thr Ala Pro Pro Ile Ser Ser Gly Pro Gly Ala Leu Ala
        355                 360                 365

Ser Val Pro Ala Ser His Pro Ala His Gly Leu Ala Pro His Glu Ser
    370                 375                 380

Gln Leu His Leu Lys Gly Asp Pro His Tyr Ser Phe Asn His Pro Phe
385                 390                 395                 400

Ser Ile Asn Asn Leu Met Ser Ser Ser Glu Gln Gln His Lys Leu Asp
                405                 410                 415

Phe Lys Ala Tyr Glu Gln Ala Leu Gln Tyr Ser Pro Tyr Gly Ser Thr
            420                 425                 430

Leu Pro Ala Ser Leu Pro Leu Gly Ser Ala Ser Val Thr Thr Arg Ser
        435                 440                 445

Pro Ile Glu Pro Ser Ala Leu Glu Pro Ala Tyr Tyr Gln Gly Val Tyr
    450                 455                 460

Ser Arg Pro Val Leu Asn Thr Ser
465                 470
```

<210> SEQ ID NO 7

```
<211> LENGTH: 2428
<212> TYPE: DNA
<213> ORGANISM: Homo sapiens
<220> FEATURE:
<221> NAME/KEY: CDS
<222> LOCATION: (186)..(1577)

<400> SEQUENCE: 7

cccgcccact tccaactacc gcctccggcc tgcccaggga gagagaggga gtggagccca     60

gggagaggga gcgcgagaga gggagggagg aggggacggt gctttggctg actttttttt    120

aaaagagggt gggggtgggg ggtgattgct ggtcgtttgt tgtggctgtt aaattttaaa    180

ctgcc atg cac tcg gct tcc agt atg ctg gga gcg gtg aag atg gaa ggg    230
      Met His Ser Ala Ser Ser Met Leu Gly Ala Val Lys Met Glu Gly
      1               5                   10                  15

cac gag ccg tcc gac tgg agc agc tac tat gca gag ccc gag ggc tac      278
His Glu Pro Ser Asp Trp Ser Ser Tyr Tyr Ala Glu Pro Glu Gly Tyr
                20                  25                  30

tcc tcc gtg agc aac atg aac gcc ggc ctg ggg atg aac ggc atg aac      326
Ser Ser Val Ser Asn Met Asn Ala Gly Leu Gly Met Asn Gly Met Asn
            35                  40                  45

acg tac atg agc atg tcg gcg gcc gcc atg ggc agc ggc tcg ggc aac      374
Thr Tyr Met Ser Met Ser Ala Ala Ala Met Gly Ser Gly Ser Gly Asn
        50                  55                  60

atg agc gcg ggc tcc atg aac atg tcg tcg tac gtg ggc gct ggc atg      422
Met Ser Ala Gly Ser Met Asn Met Ser Ser Tyr Val Gly Ala Gly Met
    65                  70                  75

agc ccg tcc ctg gcg ggg atg tcc ccc ggc gcg ggc gcc atg gcg ggc      470
Ser Pro Ser Leu Ala Gly Met Ser Pro Gly Ala Gly Ala Met Ala Gly
80                  85                  90                  95

atg ggc ggc tcg gcc ggg gcg gcc ggc gtg gcg ggc atg ggg ccg cac      518
Met Gly Gly Ser Ala Gly Ala Ala Gly Val Ala Gly Met Gly Pro His
                100                 105                 110

ttg agt ccc agc ctg agc ccg ctc ggg ggg cag gcg gcc ggg gcc atg      566
Leu Ser Pro Ser Leu Ser Pro Leu Gly Gly Gln Ala Ala Gly Ala Met
            115                 120                 125

ggc ggc ctg gcc ccc tac gcc aac atg aac tcc atg agc ccc atg tac      614
Gly Gly Leu Ala Pro Tyr Ala Asn Met Asn Ser Met Ser Pro Met Tyr
        130                 135                 140

ggg cag gcg ggc ctg agc cgc gcc cgc gac ccc aag acc tac agg cgc      662
Gly Gln Ala Gly Leu Ser Arg Ala Arg Asp Pro Lys Thr Tyr Arg Arg
    145                 150                 155

agc tac acg cac gca aag ccg ccc tac tcg tac atc tcg ctc atc acc      710
Ser Tyr Thr His Ala Lys Pro Pro Tyr Ser Tyr Ile Ser Leu Ile Thr
160                 165                 170                 175

atg gcc atc cag cag agc ccc aac aag atg ctg acg ctg agc gag atc      758
Met Ala Ile Gln Gln Ser Pro Asn Lys Met Leu Thr Leu Ser Glu Ile
                180                 185                 190

tac cag tgg atc atg gac ctc ttc ccc ttc tac cgg cag aac cag cag      806
Tyr Gln Trp Ile Met Asp Leu Phe Pro Phe Tyr Arg Gln Asn Gln Gln
            195                 200                 205

cgc tgg cag aac tcc atc cgc cac tcg ctc tcc ttc aac gac tgt ttc      854
Arg Trp Gln Asn Ser Ile Arg His Ser Leu Ser Phe Asn Asp Cys Phe
        210                 215                 220

ctg aag gtg ccc cgc tcg ccc gac aag ccc ggc aag ggc tcc ttc tgg      902
Leu Lys Val Pro Arg Ser Pro Asp Lys Pro Gly Lys Gly Ser Phe Trp
    225                 230                 235

acc ctg cac cct gac tcg ggc aac atg ttc gag aac ggc tgc tac ctg      950
Thr Leu His Pro Asp Ser Gly Asn Met Phe Glu Asn Gly Cys Tyr Leu
240                 245                 250                 255
```

```
cgc cgc cag aag cgc ttc aag tgc gag aag cag ctg gcg ctg aag gag      998
Arg Arg Gln Lys Arg Phe Lys Cys Glu Lys Gln Leu Ala Leu Lys Glu
                260                 265                 270

gcc gca ggc gcc gcc ggc agc ggc aag aag gcg gcc gcc gga gcc cag     1046
Ala Ala Gly Ala Ala Gly Ser Gly Lys Lys Ala Ala Ala Gly Ala Gln
            275                 280                 285

gcc tca cag gct caa ctc ggg gag gcc gcc ggg ccg gcc tcc gag act     1094
Ala Ser Gln Ala Gln Leu Gly Glu Ala Ala Gly Pro Ala Ser Glu Thr
        290                 295                 300

ccg gcg ggc acc gag tcg cct cac tcg agc gcc tcc ccg tgc cag gag     1142
Pro Ala Gly Thr Glu Ser Pro His Ser Ser Ala Ser Pro Cys Gln Glu
    305                 310                 315

cac aag cga ggg ggc ctg gga gag ctg aag ggg acg ccg gct gcg gcg     1190
His Lys Arg Gly Gly Leu Gly Glu Leu Lys Gly Thr Pro Ala Ala Ala
320                 325                 330                 335

ctg agc ccc cca gag ccg gcg ccc tct ccc ggg cag cag cag cag gcc     1238
Leu Ser Pro Pro Glu Pro Ala Pro Ser Pro Gly Gln Gln Gln Gln Ala
                340                 345                 350

gcg gcc cac ctg ctg ggc ccg ccc cac cac ccg ggc ctg ccg cct gag     1286
Ala Ala His Leu Leu Gly Pro Pro His His Pro Gly Leu Pro Pro Glu
            355                 360                 365

gcc cac ctg aag ccg gaa cac cac tac gcc ttc aac cac ccg ttc tcc     1334
Ala His Leu Lys Pro Glu His His Tyr Ala Phe Asn His Pro Phe Ser
        370                 375                 380

atc aac aac ctc atg tcc tcg gag cag cag cac cac cac agc cac cac     1382
Ile Asn Asn Leu Met Ser Ser Glu Gln Gln His His His Ser His His
    385                 390                 395

cac cac caa ccc cac aaa atg gac ctc aag gcc tac gaa cag gtg atg     1430
His His Gln Pro His Lys Met Asp Leu Lys Ala Tyr Glu Gln Val Met
400                 405                 410                 415

cac tac ccc ggc tac ggt tcc ccc atg cct ggc agc ttg gcc atg ggc     1478
His Tyr Pro Gly Tyr Gly Ser Pro Met Pro Gly Ser Leu Ala Met Gly
                420                 425                 430

ccg gtc acg aac aaa acg ggc ctg gac gcc tcg ccc ctg gcc gca gat     1526
Pro Val Thr Asn Lys Thr Gly Leu Asp Ala Ser Pro Leu Ala Ala Asp
            435                 440                 445

acc tcc tac tac cag ggg gtg tac tcc cgg ccc att atg aac tcc tct     1574
Thr Ser Tyr Tyr Gln Gly Val Tyr Ser Arg Pro Ile Met Asn Ser Ser
        450                 455                 460

taa gaagacgacg gcttcaggcc cggctaactc tggcaccccg gatcgaggac          1627

aagtgagaga gcaagtgggg gtcgagactt tggggagacg gtgttgcaga gacgcaaggg   1687

agaagaaatc cataacaccc ccaccccaac acccccaaga cagcagtctt cttcacccgc   1747

tgcagccgtt ccgtcccaaa cagagggcca cacagatacc ccacgttcta tataaggagg   1807

aaaacgggaa agaatataaa gttaaaaaaa agcctccggt ttccactact gtgtagactc   1867

ctgcttcttc aagcacctgc agattctgat ttttttgttg ttgttgttct cctccattgc   1927

tgttgttgca gggaagtctt acttaaaaaa aaaaaaaaat tttgtgagtg actcggtgta   1987

aaaccatgta gttttaacag aaccagaggg ttgtactatt gtttaaaaac aggaaaaaaa   2047

ataatgtaag ggtctgttgt aaatgaccaa gaaaaagaaa aaaaaagcat tcccaatctt   2107

gacacggtga aatccaggtc tcgggtccga ttaatttatg gtttctgcgt gctttattta   2167

tggcttataa atgtgtattc tggctgcaag ggccagagtt ccacaaatct atattaaagt   2227

gttatacccg gttttatccc ttgaatcttt tcttccagat tttcttttc tttacttggc    2287

ttacaaaata tacaggcttg gaaattattt caagaaggag ggagggatac cctgtctggt   2347

tgcaggttgt attttatttt ggcccaggga gtgttgctgt tttcccaaca ttttattaat   2407
```

```
aaaattttca gacataaaaa a                                              2428


<210> SEQ ID NO 8
<211> LENGTH: 463
<212> TYPE: PRT
<213> ORGANISM: Homo sapiens

<400> SEQUENCE: 8

Met His Ser Ala Ser Ser Met Leu Gly Ala Val Lys Met Glu Gly His
1               5                   10                  15

Glu Pro Ser Asp Trp Ser Ser Tyr Tyr Ala Glu Pro Glu Gly Tyr Ser
            20                  25                  30

Ser Val Ser Asn Met Asn Ala Gly Leu Gly Met Asn Gly Met Asn Thr
        35                  40                  45

Tyr Met Ser Met Ser Ala Ala Ala Met Gly Ser Gly Ser Gly Asn Met
    50                  55                  60

Ser Ala Gly Ser Met Asn Met Ser Ser Tyr Val Gly Ala Gly Met Ser
65                  70                  75                  80

Pro Ser Leu Ala Gly Met Ser Pro Gly Ala Gly Ala Met Ala Gly Met
                85                  90                  95

Gly Gly Ser Ala Gly Ala Ala Gly Val Ala Gly Met Gly Pro His Leu
            100                 105                 110

Ser Pro Ser Leu Ser Pro Leu Gly Gly Gln Ala Ala Gly Ala Met Gly
        115                 120                 125

Gly Leu Ala Pro Tyr Ala Asn Met Asn Ser Met Ser Pro Met Tyr Gly
    130                 135                 140

Gln Ala Gly Leu Ser Arg Ala Arg Asp Pro Lys Thr Tyr Arg Arg Ser
145                 150                 155                 160

Tyr Thr His Ala Lys Pro Pro Tyr Ser Tyr Ile Ser Leu Ile Thr Met
                165                 170                 175

Ala Ile Gln Gln Ser Pro Asn Lys Met Leu Thr Leu Ser Glu Ile Tyr
            180                 185                 190

Gln Trp Ile Met Asp Leu Phe Pro Phe Tyr Arg Gln Asn Gln Gln Arg
        195                 200                 205

Trp Gln Asn Ser Ile Arg His Ser Leu Ser Phe Asn Asp Cys Phe Leu
    210                 215                 220

Lys Val Pro Arg Ser Pro Asp Lys Pro Gly Lys Gly Ser Phe Trp Thr
225                 230                 235                 240

Leu His Pro Asp Ser Gly Asn Met Phe Glu Asn Gly Cys Tyr Leu Arg
                245                 250                 255

Arg Gln Lys Arg Phe Lys Cys Glu Lys Gln Leu Ala Leu Lys Glu Ala
            260                 265                 270

Ala Gly Ala Ala Gly Ser Gly Lys Lys Ala Ala Ala Gly Ala Gln Ala
        275                 280                 285

Ser Gln Ala Gln Leu Gly Glu Ala Ala Gly Pro Ala Ser Glu Thr Pro
    290                 295                 300

Ala Gly Thr Glu Ser Pro His Ser Ser Ala Ser Pro Cys Gln Glu His
305                 310                 315                 320

Lys Arg Gly Gly Leu Gly Glu Leu Lys Gly Thr Pro Ala Ala Ala Leu
                325                 330                 335

Ser Pro Pro Glu Pro Ala Pro Ser Pro Gly Gln Gln Gln Gln Ala Ala
            340                 345                 350

Ala His Leu Leu Gly Pro Pro His His Pro Gly Leu Pro Pro Glu Ala
        355                 360                 365
```

```
His Leu Lys Pro Glu His His Tyr Ala Phe Asn His Pro Phe Ser Ile
    370                 375                 380

Asn Asn Leu Met Ser Ser Glu Gln Gln His His His Ser His His His
385                 390                 395                 400

His Gln Pro His Lys Met Asp Leu Lys Ala Tyr Glu Gln Val Met His
                405                 410                 415

Tyr Pro Gly Tyr Gly Ser Pro Met Pro Gly Ser Leu Ala Met Gly Pro
            420                 425                 430

Val Thr Asn Lys Thr Gly Leu Asp Ala Ser Pro Leu Ala Ala Asp Thr
        435                 440                 445

Ser Tyr Tyr Gln Gly Val Tyr Ser Arg Pro Ile Met Asn Ser Ser
    450                 455                 460


<210> SEQ ID NO 9
<211> LENGTH: 2046
<212> TYPE: DNA
<213> ORGANISM: Homo sapiens
<220> FEATURE:
<221> NAME/KEY: CDS
<222> LOCATION: (198)..(1250)

<400> SEQUENCE: 9

ggagcccggg gcgggcgagg gcgggggtgt cccggctata aagcgtggcc gcctcccgcg      60

gcgctcggga cagccgtacc ccgggcggtc ggacgggcgg gcgccggtgg gagctcgggc     120

cgtgcccgct gagagatcca gagcgctccg ttcccccggg gccggagcgg gggcgggtgg     180

gggcgtaagc ccggggg atg ctg ggc tca gtg aag atg gag gcc cat gac        230
                   Met Leu Gly Ser Val Lys Met Glu Ala His Asp
                   1               5                   10

ctg gcc gag tgg agc tac tac ccg gag gcg ggc gag gtc tac tcg ccg       278
Leu Ala Glu Trp Ser Tyr Tyr Pro Glu Ala Gly Glu Val Tyr Ser Pro
            15                  20                  25

gtg acc cca gtg ccc acc atg gcc ccc ctc aac tcc tac atg acc ctg       326
Val Thr Pro Val Pro Thr Met Ala Pro Leu Asn Ser Tyr Met Thr Leu
        30                  35                  40

aat cct cta agc tct ccc tat ccc cct ggg ggg ctc cct gcc tcc cca       374
Asn Pro Leu Ser Ser Pro Tyr Pro Pro Gly Gly Leu Pro Ala Ser Pro
    45                  50                  55

ctg ccc tca gga ccc ctg gca ccc cca gca cct gca gcc ccc ctg ggg       422
Leu Pro Ser Gly Pro Leu Ala Pro Pro Ala Pro Ala Ala Pro Leu Gly
60                  65                  70                  75

ccc act ttc cca ggc ctg ggt gtc agc ggt ggc agc agc agc tcc ggg       470
Pro Thr Phe Pro Gly Leu Gly Val Ser Gly Gly Ser Ser Ser Ser Gly
                80                  85                  90

tac ggg gcc ccg ggt cct ggg ctg gtg cac ggg aag gag atg ccg aag       518
Tyr Gly Ala Pro Gly Pro Gly Leu Val His Gly Lys Glu Met Pro Lys
            95                  100                 105

ggg tat cgg cgg ccc ctg gca cac gcc aag cca ccg tat tcc tat atc       566
Gly Tyr Arg Arg Pro Leu Ala His Ala Lys Pro Pro Tyr Ser Tyr Ile
        110                 115                 120

tca ctc atc acc atg gcc atc cag cag gcg ccg ggc aag atg ctg acc       614
Ser Leu Ile Thr Met Ala Ile Gln Gln Ala Pro Gly Lys Met Leu Thr
    125                 130                 135

ttg agt gaa atc tac cag tgg atc atg gac ctc ttc cct tac tac cgg       662
Leu Ser Glu Ile Tyr Gln Trp Ile Met Asp Leu Phe Pro Tyr Tyr Arg
140                 145                 150                 155

gag aat cag cag cgc tgg cag aac tcc att cgc cac tcg ctg tct ttc       710
Glu Asn Gln Gln Arg Trp Gln Asn Ser Ile Arg His Ser Leu Ser Phe
                160                 165                 170
```

```
aac gac tgc ttc gtc aag gtg gcg cgt tcc cca gac aag cct ggc aag      758
Asn Asp Cys Phe Val Lys Val Ala Arg Ser Pro Asp Lys Pro Gly Lys
            175                 180                 185

ggc tcc tac tgg gcc cta cac ccc agc tca ggg aac atg ttt gag aat      806
Gly Ser Tyr Trp Ala Leu His Pro Ser Ser Gly Asn Met Phe Glu Asn
        190                 195                 200

ggc tgc tac ctg cgc cgc cag aaa cgc ttc aag ctg gag gag aag gtg      854
Gly Cys Tyr Leu Arg Arg Gln Lys Arg Phe Lys Leu Glu Glu Lys Val
    205                 210                 215

aaa aaa ggg ggc agc ggg gct gcc acc acc acc agg aac ggg aca ggg      902
Lys Lys Gly Gly Ser Gly Ala Ala Thr Thr Thr Arg Asn Gly Thr Gly
220                 225                 230                 235

tct gct gcc tcg acc acc acc ccc gcg gcc aca gtc acc tcc ccg ccc      950
Ser Ala Ala Ser Thr Thr Thr Pro Ala Ala Thr Val Thr Ser Pro Pro
                240                 245                 250

cag ccc ccg cct cca gcc cct gag cct gag gcc cag ggc ggg gaa gat      998
Gln Pro Pro Pro Pro Ala Pro Glu Pro Glu Ala Gln Gly Gly Glu Asp
            255                 260                 265

gtg ggg gct ctg gac tgt ggc tca ccc gct tcc tcc aca ccc tat ttc     1046
Val Gly Ala Leu Asp Cys Gly Ser Pro Ala Ser Ser Thr Pro Tyr Phe
        270                 275                 280

act ggc ctg gag ctc cca ggg gag ctg aag ctg gac gcg ccc tac aac     1094
Thr Gly Leu Glu Leu Pro Gly Glu Leu Lys Leu Asp Ala Pro Tyr Asn
    285                 290                 295

ttc aac cac cct ttc tcc atc aac aac cta atg tca gaa cag aca cca     1142
Phe Asn His Pro Phe Ser Ile Asn Asn Leu Met Ser Glu Gln Thr Pro
300                 305                 310                 315

gca cct ccc aaa ctg gac gtg ggg ttt ggg ggc tac ggg gct gaa ggt     1190
Ala Pro Pro Lys Leu Asp Val Gly Phe Gly Gly Tyr Gly Ala Glu Gly
                320                 325                 330

ggg gag cct gga gtc tac tac cag ggc ctc tat tcc cgc tct ttg ctt     1238
Gly Glu Pro Gly Val Tyr Tyr Gln Gly Leu Tyr Ser Arg Ser Leu Leu
            335                 340                 345

aat gca tcc tag caggggttgg gaacatggtg gtgggtatgg ctggagctca         1290
Asn Ala Ser
        350

caccacgaag ctcttggggc ctgatccttc tggtgacact tcacttgtcc cattggttaa   1350

catctgggtg ggtctattac ttactgtgat gactgctgtc tcagtgggca tggtgttgat   1410

ccacggggta ctgtgataac caccatggat acattttggt ggcccactgg gtactgtgag   1470

gactgctaca ttgatggatg ttattggcta atccactgca tggtttgatg gccaccatct   1530

cggttggccc tttgggtgtg atggtgatag catttcagtg acatcttctt tggccccccc   1590

cattaggtgc tgtgcccact tctttttgg tgtacttggc acagtaggtg ccaagttggc    1650

caccattctg tgtaacacct tttttggccc attgggtgct ttgatggaca tcatactggg   1710

taggtgacaa cgtcagtggg ccaccatgtg ccatgatggc tgctgcagcc ccgtgttggc   1770

catgtcgtca ccattctctc tggcatgggt tgggtagggg atggaggtga gaatactcct   1830

tggttttctc tgaagcccac cctttccccc aactctggtc caggagaaac cagaaaaggc   1890

tggttagggt gtggggaatt tctactgaag tctgattctt tcccgggaag cggggtactg   1950

gctgtgttta atcattaaag gtaccgtgtc cgcctcttaa aaaaaaaaaa aaaaaaaaaa   2010

aaaaaaaaaa aaaaaaaaaa aaaaaaaaaa aaaaaa                             2046
```

<210> SEQ ID NO 10
<211> LENGTH: 350
<212> TYPE: PRT

<213> ORGANISM: Homo sapiens

<400> SEQUENCE: 10

```
Met Leu Gly Ser Val Lys Met Glu Ala His Asp Leu Ala Glu Trp Ser
1               5                   10                  15

Tyr Tyr Pro Glu Ala Gly Glu Val Tyr Ser Pro Val Thr Pro Val Pro
            20                  25                  30

Thr Met Ala Pro Leu Asn Ser Tyr Met Thr Leu Asn Pro Leu Ser Ser
        35                  40                  45

Pro Tyr Pro Pro Gly Gly Leu Pro Ala Ser Pro Leu Pro Ser Gly Pro
    50                  55                  60

Leu Ala Pro Pro Ala Pro Ala Ala Pro Leu Gly Pro Thr Phe Pro Gly
65                  70                  75                  80

Leu Gly Val Ser Gly Gly Ser Ser Ser Ser Gly Tyr Gly Ala Pro Gly
                85                  90                  95

Pro Gly Leu Val His Gly Lys Glu Met Pro Lys Gly Tyr Arg Arg Pro
            100                 105                 110

Leu Ala His Ala Lys Pro Pro Tyr Ser Tyr Ile Ser Leu Ile Thr Met
        115                 120                 125

Ala Ile Gln Gln Ala Pro Gly Lys Met Leu Thr Leu Ser Glu Ile Tyr
    130                 135                 140

Gln Trp Ile Met Asp Leu Phe Pro Tyr Tyr Arg Glu Asn Gln Gln Arg
145                 150                 155                 160

Trp Gln Asn Ser Ile Arg His Ser Leu Ser Phe Asn Asp Cys Phe Val
                165                 170                 175

Lys Val Ala Arg Ser Pro Asp Lys Pro Gly Lys Gly Ser Tyr Trp Ala
            180                 185                 190

Leu His Pro Ser Ser Gly Asn Met Phe Glu Asn Gly Cys Tyr Leu Arg
        195                 200                 205

Arg Gln Lys Arg Phe Lys Leu Glu Glu Lys Val Lys Lys Gly Gly Ser
    210                 215                 220

Gly Ala Ala Thr Thr Thr Arg Asn Gly Thr Gly Ser Ala Ala Ser Thr
225                 230                 235                 240

Thr Thr Pro Ala Ala Thr Val Thr Ser Pro Pro Gln Pro Pro Pro Pro
                245                 250                 255

Ala Pro Glu Pro Glu Ala Gln Gly Gly Glu Asp Val Gly Ala Leu Asp
            260                 265                 270

Cys Gly Ser Pro Ala Ser Ser Thr Pro Tyr Phe Thr Gly Leu Glu Leu
        275                 280                 285

Pro Gly Glu Leu Lys Leu Asp Ala Pro Tyr Asn Phe Asn His Pro Phe
    290                 295                 300

Ser Ile Asn Asn Leu Met Ser Glu Gln Thr Pro Ala Pro Pro Lys Leu
305                 310                 315                 320

Asp Val Gly Phe Gly Gly Tyr Gly Ala Glu Gly Gly Glu Pro Gly Val
                325                 330                 335

Tyr Tyr Gln Gly Leu Tyr Ser Arg Ser Leu Leu Asn Ala Ser
            340                 345                 350
```

<210> SEQ ID NO 11
<211> LENGTH: 7011
<212> TYPE: DNA
<213> ORGANISM: Homo sapiens
<220> FEATURE:
<221> NAME/KEY: CDS
<222> LOCATION: (805)..(1300)
<220> FEATURE:

```
<221> NAME/KEY: CDS
<222> LOCATION: (4272)..(4867)

<400> SEQUENCE: 11

cgggccgcat cagccctcct cctgtttgcg ctccccagcg tgcaatttat ttggggggct      60

accggggatt gaacggagcg ggcgagcgct gccaggaggt ggggccggcc ccacctgtcg     120

actgcccgta gtaggcaggg agagggcggg gtttgtccca tagggcccgc cccccagtcc     180

ctgggtcccg ggcgcgcgac gagatataag gcagtcagga aacaatgcgc ctgcagctcg     240

cgctcccgcg ccgatcccga gagcgtccgg gccgccgtgc gcgagcgagg gagggcgcgc     300

gcgcgggggg ggcgcgctcg tgagtgcggg ccgcgctctc ggcggcgcgc atgtgcgtgt     360

gtgctggctg ccgggctgcc ccgagccggc ggggagccgg tccgctccag gtggcgggcg     420

gctggagcga ggtgaggctg cgggtggcca gggcacgggc gcgggtcccg cggtgcgggc     480

tggctgcagg ctgccttctg ggcacggcgc gcccccgccc ggccccgccg ggccctggga     540

gctgcgctcc gggcggcgct ggcaaagttt gctttgaact cgctgcccac agtcgggtcc     600

gcgcgctgcg attggcttcc cctaccactc tgacccgggg cccggcttcc cgggacgcga     660

ggactgggcg caggctgcaa gctggtgggg ttggggagga acgagagccc ggcagccgac     720

tgtgccgagg gacccgggga cacctccttc gcccggccgg cacccggtca gcacgtcccc     780

ccttccctcc cgcagggagc ggac atg gac tac gac tcg tac cag cac tat       831
                           Met Asp Tyr Asp Ser Tyr Gln His Tyr
                           1               5

ttc tac gac tat gac tgc ggg gag gat ttc tac cgc tcc acg gcg ccc      879
Phe Tyr Asp Tyr Asp Cys Gly Glu Asp Phe Tyr Arg Ser Thr Ala Pro
10                  15                  20                  25

agc gag gac atc tgg aag aaa ttc gag ctg gtg cca tcg ccc ccc acg      927
Ser Glu Asp Ile Trp Lys Lys Phe Glu Leu Val Pro Ser Pro Pro Thr
                30                  35                  40

tcg ccg ccc tgg ggc ttg ggt ccc ggc gca ggg gac ccg gcc ccc ggg      975
Ser Pro Pro Trp Gly Leu Gly Pro Gly Ala Gly Asp Pro Ala Pro Gly
            45                  50                  55

att ggt ccc ccg gag ccg tgg ccc gga ggg tgc acc gga gac gaa gcg     1023
Ile Gly Pro Pro Glu Pro Trp Pro Gly Gly Cys Thr Gly Asp Glu Ala
        60                  65                  70

gaa tcc cgg ggc cac tcg aaa ggc tgg ggc agg aac tac gcc tcc atc     1071
Glu Ser Arg Gly His Ser Lys Gly Trp Gly Arg Asn Tyr Ala Ser Ile
    75                  80                  85

ata cgc cgt gac tgc atg tgg agc ggc ttc tcg gcc cgg gaa cgg ctg     1119
Ile Arg Arg Asp Cys Met Trp Ser Gly Phe Ser Ala Arg Glu Arg Leu
90                  95                  100                 105

gag aga gct gtg agc gac cgg ctc gct cct ggc gcg ccc cgg ggg aac     1167
Glu Arg Ala Val Ser Asp Arg Leu Ala Pro Gly Ala Pro Arg Gly Asn
                110                 115                 120

ccg ccc aag gcg tcc gcc gcc ccg gac tgc act ccc agc ctc gaa gcc     1215
Pro Pro Lys Ala Ser Ala Ala Pro Asp Cys Thr Pro Ser Leu Glu Ala
            125                 130                 135

ggc aac ccg gcg ccc gcc gcc ccc tgt ccg ctg ggc gaa ccc aag acc     1263
Gly Asn Pro Ala Pro Ala Ala Pro Cys Pro Leu Gly Glu Pro Lys Thr
        140                 145                 150

cag gcc tgc tcc ggg tcc gag agc cca agc gac tcg g gtaaggacct        1310
Gln Ala Cys Ser Gly Ser Glu Ser Pro Ser Asp Ser
    155                 160                 165

ccccgagcca tccaagaggg ggccacccca tgggtggcca aagctctgcc cctgcctgag   1370

gtcaggcatt ggctcttctc aagctcttgg gccatctccg cctctctttg gctgaagctg   1430
```

-continued

```
cccgtgtagt ccccaaccgt gtctgtctgg cacgtgggtg tgttggtaaa cagtttggaa   1490
aagtggcgtg ggagccagcc tccctttgat gattattgga gccccagggg acaagggatt   1550
tgaggtgagg gttggcgctt agagaggaca atactggggt tggactgtaa gggattgaag   1610
ggggtacctt aagagacact ccaaacctga agtttttttg ctgctgcctc tttccctagg   1670
aaactcacac tcccctaggg ggagaagaag ccgagagcct tttgtgcaaa gccaaaacct   1730
tcgtcctttt aaaaacctag gtctccagtt ggctttactt taaaatgcca ataataaatg   1790
ccctcttctc gtgcctcccc accaccactt accactcgtg catccctgag acagggaggg   1850
aagaatgaac actccccatt aacagatgga aaaactgagg cttagagata gacaatcact   1910
acaagtcagc tccagctttc tgccatctag ccagcccctc ttccccaatg ctccatccca   1970
accaggcacc tcttccttga tgtttggggt ctttgtggta gcttatctta gaagcactac   2030
accttgcctt gctgtttgtc ctgagatgga aaagtgtcct tcttgctccc cctcaataga   2090
tctccagcgt cagctgctcc ctggcattca acaaatattc actggcccct actttgtggc   2150
aatctgtggg ctacatgctg ggtcaaggc agtagaactc caggccctcc tctcccatcc   2210
ttgatgcaag tgcaacctcg ctgagggcag actggggcat cctgtgccac taaactacat   2270
tgttcttatt ctggcatctt agacctccac acccgtgaga aatcctggag agggtatttt   2330
tgtagagtgt agactgtggc tagtgacaaa taaattagga ccaagaaagc tcactgtagc   2390
ttttaggaat aacttttaca cgaccatttg atagggaact ggggaatggg gtatggaagt   2450
tttcctacac ttgagagaaa aaataggata acaaaaatta aaagtctttt tttcctggtc   2510
cactgtgtta aggtcatttt taaccagctt gctttctaca ccaagagttt atgtttgttt   2570
aatggctgga aagagaatct tgagatcaaa aaaccaataa agatgtatct ctacaacggc   2630
tggtggagtg gtagagtgga aagagcattg ctttggaagt tggaacattt tagtttgaga   2690
tccagaacgt tacaaaggtg atatgtggac ttcgctgatc tgggcctcag tttccccatt   2750
tgcacacgat ggggttggac ttgattgtcc tgctgatgac atttccttgt ctggatagag   2810
taagacacta ctctctgaaa gggagaatgg tgtgcttaaa ttatttcttt cttagataga   2870
atcttcctga gccacgaggc ttaacactga aaattaaagg tttgggatgt aggaaagcct   2930
gctgaatcat tttctaacct accctttaac ctgaacctgt ttgtgagctt ctagttcact   2990
cacaggccac atggcctgga acaaaatgca acagattgca aacaatgagg cggggggtgg   3050
ggaaagtgat tggcagcaga gctcacccaa taggggctag gggctgggta agacagaatt   3110
ccaaacacag cgtaatcagc caatcatggg ctttggggcc aggagggctg aatggtcagg   3170
tttattaatg gagaaataat gcgattgtcc acacaatgga agccttcctg acaaaggggc   3230
tcaagcttcc tgatatgcaa agaagctgag aacggagctc ttcctttgcc gaggccgaga   3290
tccattaagg tcggacttct gtgtggaggc tgcaaaatgt gtggagcagg aggagacttt   3350
tctcccaatt gcccctctcc tggttaggtt aacctaagag accttcaagc cagtgaatga   3410
gaagggcgtg tccaggtgtc tccaggtctc tggtgttatg agccccatat ctgggacatt   3470
ctgctgccca gtctctgcct ctggtgcagg tagtttggaa atggtcgctt gtacctttgt   3530
gaagttcctg cagcttcgcc gacctatgat tacaaatcta accttctagt ccagggaagg   3590
aggtggggca ggcgacctat aaatgatgga tgactttaga aacccattga acccaggagc   3650
aaaatgctcc taagggaaac cctttccctc ccctctgtgg gtgaagaggg atgggttgta   3710
gccctccctt ctctgaatct tcagctgaaa gggatggcag aatagagagg tgggggaata   3770
ataggattta taacttgtga aaagtaacaa ttccccaagt gcaggctgtg ctgggcagga   3830
```

```
acaaagggca gctctgccca cagacccctc atttacaatt ctgatggggc atgaaagagc   3890

ccgactgggg aagatcttta tagctaaact ttgtcccagg ccggtagctc tttctctcca   3950

acccctccgt gggggagggg agagcctttg cagactgggg gctgttggct tgggtctgcc   4010

ttttgttctt atctaagcct tgctgtgcaa aaggaaattg gagaatattt tccttcttgc   4070

taatgtcccc tcctttcctt cactgtgccc ttaccacatt acaaatgaat cagctttctg   4130

ctcacctcga tttgtatata tctaaattgg aaaaatgtct cctaccttcc caagcaccag   4190

cgtagacagc taaagctgta gggtctatgt ttgtgtttct catgggatgt gtttcttctc   4250

ttgatctctt ttctcggaca g ag  aat gaa gaa att gat gtt gtg aca gta     4300
                        Glu Asn Glu Glu Ile Asp Val Val Thr Val
                                        170                 175

gag aag agg cag tct ctg ggt att cgg aag ccg gtc acc atc acg gtg     4348
Glu Lys Arg Gln Ser Leu Gly Ile Arg Lys Pro Val Thr Ile Thr Val
                180                 185                 190

cga gca gac ccc ctg gat ccc tgc atg aag cat ttc cac atc tcc atc     4396
Arg Ala Asp Pro Leu Asp Pro Cys Met Lys His Phe His Ile Ser Ile
            195                 200                 205

cat cag caa cag cac aac tat gct gcc cgt ttt cct cca gaa agc tgc     4444
His Gln Gln Gln His Asn Tyr Ala Ala Arg Phe Pro Pro Glu Ser Cys
        210                 215                 220

tcc caa gaa gag gct tca gag agg ggt ccc caa gaa gag gtt ctg gag     4492
Ser Gln Glu Glu Ala Ser Glu Arg Gly Pro Gln Glu Glu Val Leu Glu
    225                 230                 235

aga gat gct gca ggg gaa aag gaa gat gag gag gat gaa gag att gtg     4540
Arg Asp Ala Ala Gly Glu Lys Glu Asp Glu Glu Asp Glu Glu Ile Val
240                 245                 250                 255

agt ccc cca cct gta gaa agt gag gct gcc cag tcc tgc cac ccc aaa     4588
Ser Pro Pro Pro Val Glu Ser Glu Ala Ala Gln Ser Cys His Pro Lys
                260                 265                 270

cct gtc agt tct gat act gag gat gtg acc aag agg aag aat cac aac     4636
Pro Val Ser Ser Asp Thr Glu Asp Val Thr Lys Arg Lys Asn His Asn
            275                 280                 285

ttc ctg gag cgc aag agg cgg aat gac ctg cgt tcg cga ttc ttg gcg     4684
Phe Leu Glu Arg Lys Arg Arg Asn Asp Leu Arg Ser Arg Phe Leu Ala
        290                 295                 300

ctg agg gac cag gtg ccc acc ctg gcc agc tgc tcc aag gcc ccc aaa     4732
Leu Arg Asp Gln Val Pro Thr Leu Ala Ser Cys Ser Lys Ala Pro Lys
    305                 310                 315

gta gtg atc cta agc aag gcc ttg gaa tac ttg caa gcc ctg gtg ggg     4780
Val Val Ile Leu Ser Lys Ala Leu Glu Tyr Leu Gln Ala Leu Val Gly
320                 325                 330                 335

gct gag aag agg atg gct aca gag aaa aga cag ctc cga tgc cgg cag     4828
Ala Glu Lys Arg Met Ala Thr Glu Lys Arg Gln Leu Arg Cys Arg Gln
                340                 345                 350

cag cag ttg cag aaa aga att gca tac ctc ast ggc tac taactgacca      4877
Gln Gln Leu Gln Lys Arg Ile Ala Tyr Leu Xaa Gly Tyr
            355                 360

aaaagcctga cagttctgtc ttacgaagac acaagtttat tttttaacct ccctctcccc   4937

tttagtaatt tgcacatttt ggttatggtg ggacagtctg gacagtagat cccagaatgc   4997

attgcagccg gtgcacacac aataaaggct tgcattcttg gaaaccttga aacccagctc   5057

tccctcttcc ctgactcatg ggagtgctgt atgttctctg gcgcctttgg cttcccagca   5117

ggcagctgac tgaggagcct tggggtctgc ctagctcact agctctgaag aaaaggctga   5177

cagatgctat gcaacaggtg gtggatgttg tcaggggctc cagcctgcat gaaatctcac   5237
```

```
actctgcatg agctttaggc taggaaagga tgctcccaac tggtgtctct ggggtgatgc   5297

aaggacagct gggcctggat gctctccctg aggctccttt ttccagaaga cacacgagct   5357

gtcttgggtg aagacaagct tgcagacttg atcaacattg accattacct cactgtcaga   5417

cactttacag tagccaagga gttggaaacc tttatgtatt atgatgttag ctgacccccct   5477

tcctcccact cccaatgctg cgaccctggg aacacttaaa aagcttggcc tctagattct   5537

ttgtctcaga gccctctggg ctctctcctc tgagggaggg acctttcttt cctcacaagg   5597

gactttttg ttccattatg ccttgttatg caatgggctc tacagcaccc tttcccacag   5657

gtcagaaata tttccccaag acacagggaa atcggtccta gcctggggcc tggggatagc   5717

ttggagtcct ggcccatgaa cttgatccct gcccaggtgt tttccgaggg gcacttgagg   5777

cccagtcttt tctcaaggca ggtgtaagac actcagaggg agaactgtac tgctgcctct   5837

ttcccacctt cctcatctca atccttgagc ggcaagtttg aagttcttct ggaaccatgc   5897

aaatctgtcc tcctcatgca attccaagga gcttgctggc tctgcagcca cctctgggcc   5957

ccttccagcc tgccatgaat cagatatctt tcccagaatc tgggcgtttc tgaagttttg   6017

gggagagctg ttgggactca tccagtgctc cagaaggtgg acttgcttct gggggggtttt   6077

aaaggagcct ccaggagata tgcttagcca accatgatgg attttacccc agctggactc   6137

ggcagctcca agtggaatcc acgtgcagct tctagtctgg gaaagtcacc caacctagca   6197

gttgtcatgt gggtaacctc aggcacctct aagcctgtcc tggaagaagg accagcagcc   6257

cctccagaac tctgcccagg acagcaggtg cctgctggct ctgggtttgg aagtttgggg   6317

tgggtagggg gtggtaagta ctatatatgg ctctggaaaa ccagctgcta cttccaaatc   6377

tattgtccat aatggtttct ttctgaggtt gcttcttggc ctcagaggac cccaggggat   6437

gtttggaaat agcctctcta cccttctgga gcatggttta caaaagccag ctgacttctg   6497

gaattgtcta tggaggacag tttgggtgta ggttactgat gtctcaactg aatagcttgt   6557

gttttataag ctgctgttgg ctattatgct gggggagtct ttttttttta tattgtattt   6617

ttgtatgcct tttgcaaagt ggtgttaact gtttttgtac aaggaaaaaa actcttgggg   6677

caatttcctg ttgcaagggt ctgatttatt ttgaaaggca agttcacctg aaattttgta   6737

tttagttgtg attactgatt gcctgatttt aaaatgttgc cttctgggac atcttctaat   6797

aaaagatttc tcaaacatgt cagagtgggg gcagcttatg ccacctgagt cctcctcaac   6857

cacggaaaac tatttcaggg tagccacaag tgatccagag ggctgcactt ctctaaccat   6917

gttgctaacc tggtcattcc actctgggtt cctgaaatgc catttcagac atgttgaaac   6977

aatgtaggct cagtactcag tgaacacgga attc                               7011
```

```
<210> SEQ ID NO 12
<211> LENGTH: 364
<212> TYPE: PRT
<213> ORGANISM: Homo sapiens
<220> FEATURE:
<221> NAME/KEY: misc_feature
<222> LOCATION: (362)..(362)
<223> OTHER INFORMATION: The 'Xaa' at location 362 stands for Ser, or
      Thr.

<400> SEQUENCE: 12

Met Asp Tyr Asp Ser Tyr Gln His Tyr Phe Tyr Asp Tyr Asp Cys Gly
1               5                   10                  15

Glu Asp Phe Tyr Arg Ser Thr Ala Pro Ser Glu Asp Ile Trp Lys Lys
            20                  25                  30
```

-continued

```
Phe Glu Leu Val Pro Ser Pro Pro Thr Ser Pro Pro Trp Gly Leu Gly
        35                  40                  45

Pro Gly Ala Gly Asp Pro Ala Pro Gly Ile Gly Pro Pro Glu Pro Trp
    50                  55                  60

Pro Gly Gly Cys Thr Gly Asp Glu Ala Glu Ser Arg Gly His Ser Lys
65                  70                  75                  80

Gly Trp Gly Arg Asn Tyr Ala Ser Ile Ile Arg Arg Asp Cys Met Trp
                85                  90                  95

Ser Gly Phe Ser Ala Arg Glu Arg Leu Glu Arg Ala Val Ser Asp Arg
            100                 105                 110

Leu Ala Pro Gly Ala Pro Arg Gly Asn Pro Pro Lys Ala Ser Ala Ala
        115                 120                 125

Pro Asp Cys Thr Pro Ser Leu Glu Ala Gly Asn Pro Ala Pro Ala Ala
    130                 135                 140

Pro Cys Pro Leu Gly Glu Pro Lys Thr Gln Ala Cys Ser Gly Ser Glu
145                 150                 155                 160

Ser Pro Ser Asp Ser Glu Asn Glu Glu Ile Asp Val Val Thr Val Glu
                165                 170                 175

Lys Arg Gln Ser Leu Gly Ile Arg Lys Pro Val Thr Ile Thr Val Arg
            180                 185                 190

Ala Asp Pro Leu Asp Pro Cys Met Lys His Phe His Ile Ser Ile His
        195                 200                 205

Gln Gln Gln His Asn Tyr Ala Ala Arg Phe Pro Pro Glu Ser Cys Ser
    210                 215                 220

Gln Glu Glu Ala Ser Glu Arg Gly Pro Gln Glu Glu Val Leu Glu Arg
225                 230                 235                 240

Asp Ala Ala Gly Glu Lys Glu Asp Glu Glu Asp Glu Glu Ile Val Ser
                245                 250                 255

Pro Pro Pro Val Glu Ser Glu Ala Ala Gln Ser Cys His Pro Lys Pro
            260                 265                 270

Val Ser Ser Asp Thr Glu Asp Val Thr Lys Arg Lys Asn His Asn Phe
        275                 280                 285

Leu Glu Arg Lys Arg Arg Asn Asp Leu Arg Ser Arg Phe Leu Ala Leu
    290                 295                 300

Arg Asp Gln Val Pro Thr Leu Ala Ser Cys Ser Lys Ala Pro Lys Val
305                 310                 315                 320

Val Ile Leu Ser Lys Ala Leu Glu Tyr Leu Gln Ala Leu Val Gly Ala
                325                 330                 335

Glu Lys Arg Met Ala Thr Glu Lys Arg Gln Leu Arg Cys Arg Gln Gln
            340                 345                 350

Gln Leu Gln Lys Arg Ile Ala Tyr Leu Xaa Gly Tyr
        355                 360
```